US006964661B2

(12) United States Patent
Rioux et al.

(10) Patent No.: US 6,964,661 B2
(45) Date of Patent: Nov. 15, 2005

(54) ENDOVENOUS ABLATION MECHANISM WITH FEEDBACK CONTROL

(75) Inventors: Robert F. Rioux, Ashland, MA (US); Paul DiCarlo, Middleboro, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 113 days.

(21) Appl. No.: 10/406,074

(22) Filed: Apr. 2, 2003

(65) Prior Publication Data

US 2004/0199156 A1 Oct. 7, 2004

(51) Int. Cl.[7] .............................................. A61B 18/18
(52) U.S. Cl. ........................ 606/41; 606/42; 600/486; 128/898
(58) Field of Search ..................... 606/27–34, 41–52; 607/101, 102; 600/486, 488; 128/898

(56) References Cited

U.S. PATENT DOCUMENTS

| | | | |
|---|---|---|---|
| 5,083,573 A | | 1/1992 | Arms |
| 5,222,953 A | * | 6/1993 | Dowlatshahi ................ 606/15 |
| 5,447,161 A | | 9/1995 | Blazek et al. |
| 6,033,401 A | * | 3/2000 | Edwards et al. .............. 606/41 |
| 6,077,261 A | | 6/2000 | Behl et al. |
| 6,096,054 A | | 8/2000 | Wyzgala et al. |
| 6,165,172 A | | 12/2000 | Farley et al. |
| 6,179,832 B1 | * | 1/2001 | Jones et al. ................... 606/32 |
| 6,267,758 B1 | * | 7/2001 | Daw et al. ..................... 606/42 |
| 2002/0123749 A1 | * | 9/2002 | Jain ............................. 606/41 |
| 2002/0198547 A1 | | 12/2002 | Schultz |
| 2003/0191460 A1 | * | 10/2003 | Hobbs et al. ................ 606/15 |
| 2004/0243007 A1 | * | 12/2004 | Tenerz et al. ............... 600/486 |

FOREIGN PATENT DOCUMENTS

EP 6 069 914 A2 8/1994

OTHER PUBLICATIONS

PCT International Search Report for PCT/US04/005600, Applicant: Scimed Life Systems, Inc., Forms PCT/ISA/210 and 220, dated Jun. 21, 2004 (6 pages).
PCT Written Opinion of the International Search Authority for PCT/US04/005600, Applicant: Scimed Life Systems, Inc., Form PCT/ISA/237, dated Jun. 21, 2004 (5 pages).

* cited by examiner

*Primary Examiner*—Michael Peffley
(74) *Attorney, Agent, or Firm*—Bingham McCutchen LLP

(57) ABSTRACT

A vessel occlusion system includes one or more ablation elements that, when activated, is configured for at least partially closing a vessel segment of a patient. The vessel occlusion system further includes a sensor assembly that is configured for generating feedback indicative of a state of closure of the vessel segment, and an automated longitudinal translator configured for longitudinally translating the one or more ablation elements based on the feedback from the sensor assembly. The one or more ablation elements may be associated with a catheter member that slides within the catheter sheath.

20 Claims, 16 Drawing Sheets

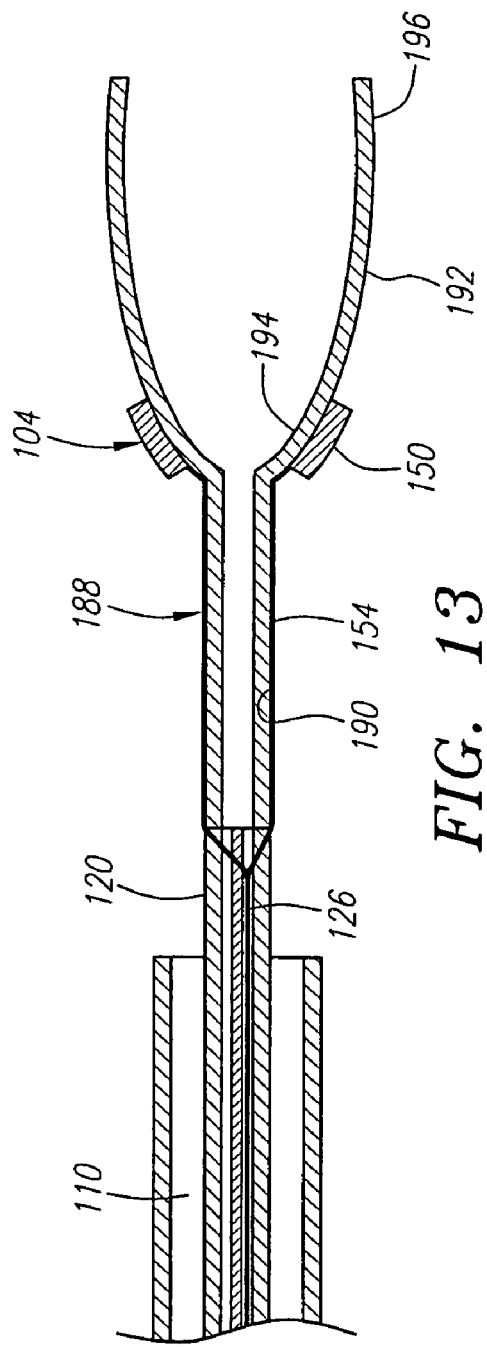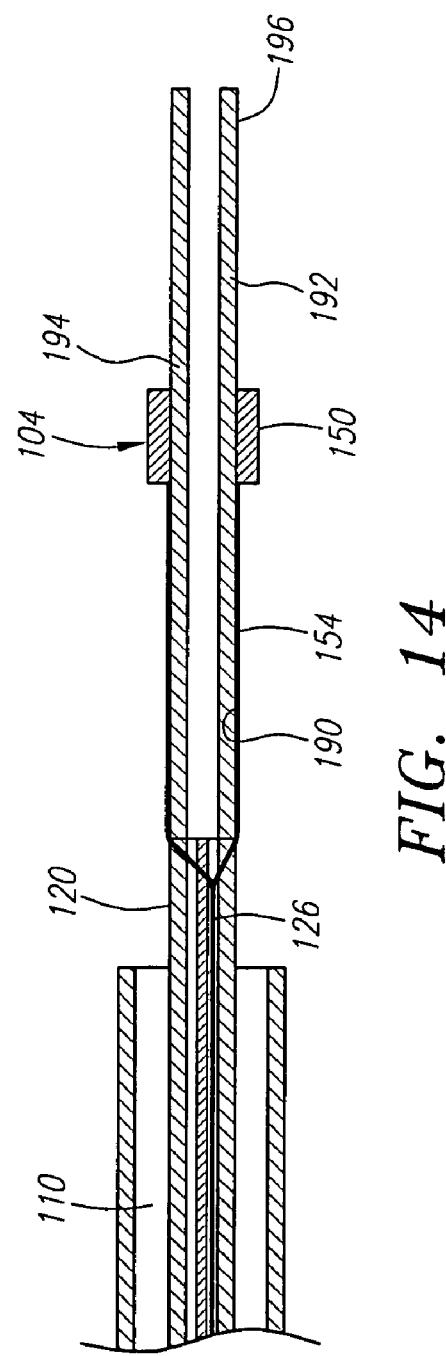
FIG. 13
FIG. 14

ENDOVENOUS ABLATION MECHANISM WITH FEEDBACK CONTROL

FIELD OF THE INVENTION

The field of the invention relates generally to methods and devices for the selective occlusion of body lumens.

BACKGROUND OF THE INVENTION

The selective occlusion of blood vessels in a patient is a part of many modern therapeutic treatments, including the control of internal bleeding, the occlusion of blood supply to tumors, the isolation of diseased body organs prior to removal, the relief of blood pressure in an aneurysm, and the like. While such procedures rely generally on the blockage of arteries, the selective occlusion of veins is also useful in procedures, such as veiniotomy.

The occlusion of blood vessels can be achieved using a variety of specific techniques. For example, chemical occlusion of blood vessels is typically accomplished by introduction of a non-physiological solution into the vessel lumen. The solution is selected to destroy the endothelial wall and injure the underlying tissue, causing edema, fibrin deposition, and eventually fibrosis of the lumen. In addition to the use of such chemical agents, e.g., ethanol, tetradecyl sulfate, and hypertonic saline, heat can also be applied to induce fibrosis of the lumen.

Laser occlusion of blood vessels can be accomplished by introducing the end of a laser fiber within the blood vessel, and transmitting laser energy from the end of the fiber into the endothelial wall of the vessel. For example, Diomed, Inc., located in Andover, Mass., markets a laser-based varicose vein treatment system under the trademark EVLT™ (EndoVenous Laser Treatment).

Radio frequency (RF) occlusion of blood vessels can be accomplished by introducing one or more electrodes into contact with the endothelial of the blood vessel, and conveying RF energy to the electrodes. Exemplary RF devices are disclosed in U.S. Pat. No. 6,077,261, entitled "Device For Permanent Vessel Occlusion," and U.S. Pat. No. 6,165,172, entitled "Expandable Vein Ligator Catheter and Method of Use."

The various RF ablation devices disclosed in U.S. Pat. No. 6,077,261 utilize mechanical endoluminal devices that collapse the vessel wall to bring opposing portions of the endothelial wall of the blood vessel partially or completely together. RF energy is then applied to one or more electrodes within the occlusion region between the opposed wall portions to injure or destroy the endothelial cells and underlying tissue in the occlusion region, and initiating a process of thrombosis and fibrosis, which will result in relatively rapid vessel occlusion. Mechanical closure of the endothelial wall slows or stops the flow of blood, greatly enhancing the rate of thermal transfer, which in turn enhances the rate of fibrosis and thrombosis. The RF ablation devices disclosed in U.S. Pat. No. 6,165,172 utilizes a plurality of spoon-shaped electrodes that are circumferentially disposed around the endothelial vessel wall when deployed to provide a uniform distribution of energy and more predictable and efficient occlusion of the vessel. The control system is programmed to maintain the endothelial wall of the blood vessel at a constant temperature, e.g., 85° C., to ensure cross-sectional shrinkage of the blood vessel. A balloon can be used to occlude the blood flow. A commercial embodiment of this type of system is marketed by VNUS Medical Technologies, Inc. under the trademark Closure®.

The above-described vessel occlusion systems allow for the pullback of the relevant ablation device within a sheath as the vessel closes, thereby producing a longitudinal occlusion, which is stronger and less susceptible to recanalization than an acute point occlusion. Venous ablation methods are prone to complications due to technique requirements. Such complications include, but are not limited to incomplete vessel closure, numbness, skin burns, and infection. The major causes of these complications are related to the pullback rate and determining if the vessel is closed. Thus, the ablation device is preferably pulled back at a speed that assures vessel closure.

For example, if the pullback speed of the RF electrodes in the Closure® vessel occlusion system is too rapid, the RF generator will be driven towards the maximum wattage. If this occurs, thermal penetration to the high-collagen-content adventitia can become compromised, resulting in endothelial searing without optimal vein-wall contraction. Slow pull back in the range of 2.5 to 3.5 cm/min, and a thorough post-treatment ultrasound assessment of the entire treated vessel, combined with occasional retreatment of incompletely contracted segments of the vessel should greatly diminish the incidence of early treatment failures. The laser in the EVLT™ should have a slow pull back in the range of 2 to 3 mm/second. Constant compression of the vessel is required to minimize the distance from the laser fiber to the endothelial vessel wall to assure completion ablation/closure of the vessel.

In both the Closure® and EVLT™ venous ablation systems, the physician must pullback the ablation devices manually, and thus, improper pullback can cause incomplete vessel closure or surrounding tissue damage.

Thus, there is a need for an improved venous ablation system and method that assures, or at least maximizes the chance, that vessel closure will be achieved.

SUMMARY OF THE INVENTION

The present inventions are directed to vessel occlusion systems and methods for occluding vessels, such as, e.g., blood vessels.

In accordance with a first aspect of the present inventions, a method of occluding a vessel (such as, e.g., a blood vessel) comprises ablating an endothelial wall of a vessel segment by activating a single ablation element or multiple ablation elements, and sensing a closing of the vessel segment, generating feedback (e.g., electrical, electromagnetic, mechanical, pneumatic, hydraulic, or any combination thereof) indicating a state of closure of the vessel segment. The method may optionally comprises automatically longitudinally translating the ablation element(s) relative to the vessel segment based on the feedback. Various forms of ablation can be used, e.g., RF energy, microwave energy, laser energy, or chemical solution. The vessel segment can be partially or completely closed.

In the preferred method, the sensed vessel segment closure state is compared to a closed vessel threshold, and the ablation element(s) is translated in a proximal direction when the vessel segment closure state equals the closed vessel threshold. The sensed vessel segment closure state is also compared to an open vessel threshold, and longitudinal translation of the ablation element(s) in the proximal direction is ceased when the vessel segment closure state equals the vessel open threshold. An acute point occlusion can be created by occluding only one vessel segment, or a longitudinal occlusion can be created by repeating the endothelial wall ablation, vessel segment closure sensing, feedback generation, and automatic longitudinal translation for the next proximal vessel segment.

In accordance with a second aspect of the present inventions, a vessel occlusion system comprises a single ablation element or multiple ablation elements, which when activated, is configured for at least partially closing a vessel segment of a patient. The ablation element can take the form of any element that is suitable for occluding a vessel segment using ablation. For example, the ablation element can comprise a radio frequency (RF) or microwave electrode, a laser fiber, or a chemical actuating element (e.g., an element that releases chemicals or one that mixes chemicals to generate thermal energy).

The vessel occlusion system further comprises a sensor assembly configured for generating feedback indicative of a state of closure of the vessel segment. The feedback can be, e.g., completely mechanical, electrical, electromagnetic, pneumatic, hydraulic or a combination thereof. The sensor assembly can comprise a single sensor or multiple sensors that can be either distally or proximally located. The sensor(s) can be located anywhere relative to the device that allows it to directly or indirectly sense the closing of the vessel segment. For example, the sensor(s) can be located on the ablation element(s) or on the distal or proximal end of a catheter member or catheter sheath associated with the ablation element(s). In the preferred embodiment, the sensor(s) can comprise strain gages configured for generating a signal indicate of a strain directly or indirectly applied to the strain gage by the vessel. For example, if the strain gage is distally located, the closed vessel segment may directly apply strain to the strain gage, and the strain gage can generate an electrical feedback signal. If the strain gage is proximally located, the closed vessel segment may indirectly apply strain to the strain gage, e.g., via a distally disposed compressible membrane and a medium filled lumen in communication with the compressible membrane, so that the lumen conveys a medium indicative of a pressure applied to the compressible membrane by the vessel segment. The strain gage generates an electrical feedback signal based on the mechanical feedback signal from the pressure indicating medium. Alternatively, the sensors can comprise other types of sensors, such as temperature sensors, impedance sensors, or ultrasound echoing transducers.

The vessel occlusion system optionally comprises an automated longitudinal translator configured for longitudinally translating the one or more ablation elements based on the feedback from the sensor assembly. By way of non-limiting example, the automated longitudinal translator can be configured for longitudinally translating the one or more ablation elements in a proximal direction when the vessel segment closure state indicated by the feedback from the sensor assembly equals a closed vessel threshold, and ceasing the longitudinal translation of the one or more ablation elements in the proximal direction when the feedback from the sensor assembly equals an open vessel threshold. The automated longitudinal translator comprises any suitable mechanism, e.g., a pump, that can automate the movement of the ablation element(s).

In the preferred embodiment, the vessel occlusion system may comprise a catheter sheath, in which case, the optional automated longitudinal translator may be configured for longitudinally translating the element(s) relative to the catheter sheath. The automated longitudinal translator can be either internal or external to the catheter sheath. The vessel occlusion system may further comprise a catheter member slidably disposed within the catheter sheath, wherein the ablation element(s) is associated with the catheter member For example, the ablation element(s) may be mounted to the distal end of the catheter member or can be disposed within the catheter member. In this case, the automated longitudinal translator can be configured for longitudinally translating the catheter member relative to the catheter sheath. Alternatively, rather than using a catheter member, the ablation element(s) can be directly associated with the catheter sheath.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 13 illustrates a cross-sectional view of an alternative ablation element that can be used with the vessel occlusion system of FIG. 1, particularly showing the ablation element in its expanded state;

FIG. 14 illustrates a cross-sectional view the ablation element of FIG. 13, particularly showing the ablation element in its collapsed state.

DETAILED DESCRIPTION OF THE PREFERRED EMBODIMENTS

Figure 1:
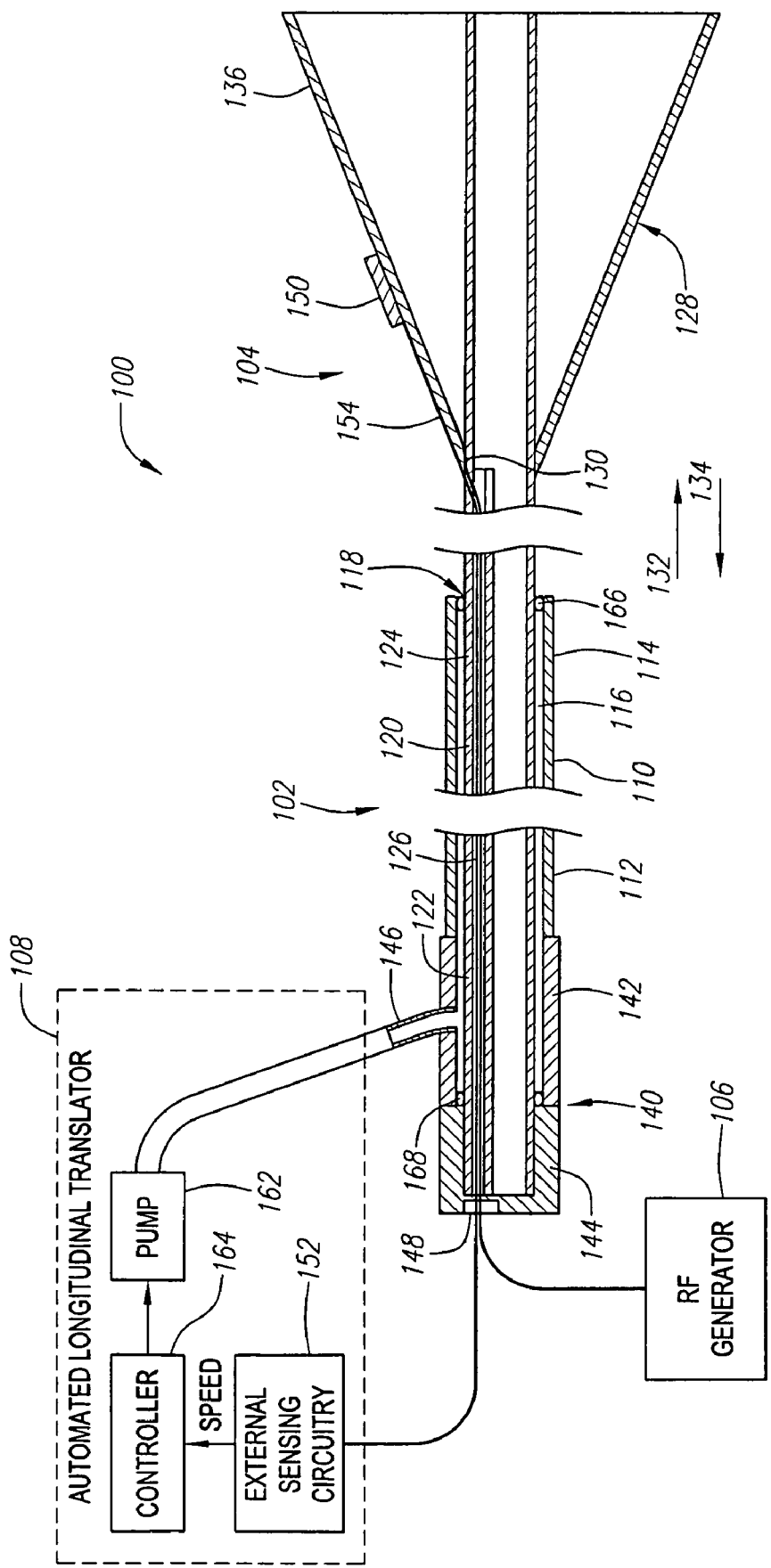
FIG. 1 illustrates a vessel occlusion system constructed in accordance with one preferred embodiment of the present inventions, wherein a catheter assembly used with the vessel occlusion system is particularly shown in cross-section with the ablation electrode in its deployed state.

FIG. 1 illustrates a vessel occlusion system 100 constructed in accordance with a preferred embodiment of the present inventions. The vessel occlusion system 100 generally comprises a vessel occlusion catheter assembly 102, a sensor assembly 104, a radio frequency (RF) generator 106, and an automated longitudinal translator 108.

The catheter assembly 102 generally comprises an elongated outer catheter sheath 110 having a proximal end 112, a distal end 114, and a central lumen 116 extending through the catheter sheath 110 between the proximal end 112 and an axial opening 118 located at the distal end 114. The catheter sheath 110 has a suitable length, typically in the range from 40 cm to 200 cm, usually from 75 cm to 120 cm. The catheter sheath 110 has an outside diameter consistent with its intended use, typically being from 1 mm to 5 mm, usually from 2 mm to 4 mm. The catheter sheath 110 includes means for introducing the sheath 110 over a movable guide wire 180 (shown in FIG. 5B). In the illustrated embodiment, the guide wire 180 will run through the central lumen 116 to provide an "over-the-wire" design. Alternatively, the catheter sheath 110 may have a "rapid exchange" or "monorail" design, in which case, the guide wire 180 can be received through a lumen (not shown) that extends only over a distal length of the catheter sheath 110, typically from 5 cm to 25 cm.

The catheter sheath 110 may be composed of a variety of conventional catheter materials, including natural and synthetic polymers, such as polyvinyl chloride, polyurethanes, polyesters, polyethylenes, polytetrafluoroethylenes (PTFE's), nylons, and the like. The catheter sheath 110 may optionally be reinforced to enhance its strength, torqueability, and the like. Exemplary reinforcement layers include metal fiber braids, polymeric fiber braids, metal or fiber helical windings, and the like. Optionally, a portion of the catheter sheath 110 could be formed from a metal rod or hypotube, particularly when the catheter sheath 110 has a rapid exchange or monorail design.

The catheter assembly 102 further comprises an elongated catheter member 120 having a proximal end 122, a distal end 124, and a wire lumen 126 extending through the catheter member 120 between the proximal and distal ends 122 and 124. The catheter member 120 is slidably disposed within the central lumen 116 of the catheter sheath 110. The catheter assembly 102 further comprises an expandable/collapsible RF ablation electrode 128 mounted to the distal end 122 of the catheter member 120. Accordingly, one or more RF wires 130 extends through the wire lumen 124 and is suitably coupled to the RF ablation electrode 128, e.g., soldering. The catheter member 120 is composed of a suitable rigid material, e.g., the same material of which the catheter sheath 110 is composed. Alternatively, the catheter member 120 can be composed of an electrically conductive material, such as, e.g., stainless steel, in which case, it can act as an RF electrical conductor, obviating the need for separate RF wires.

Figure 15:
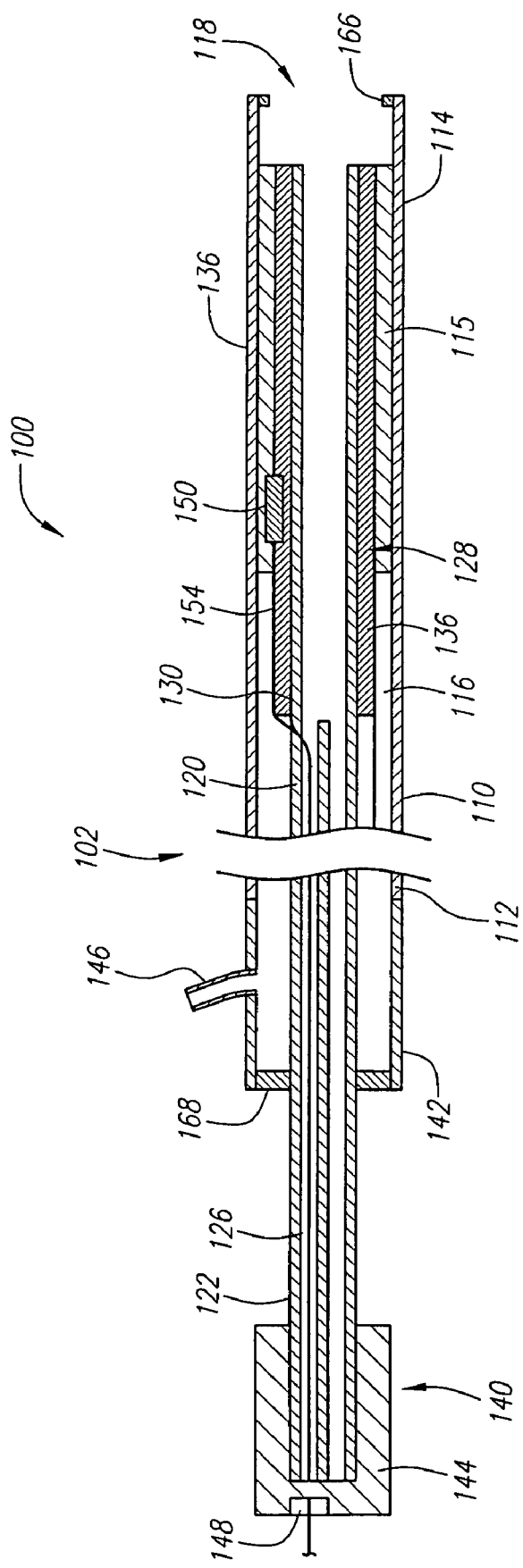
FIG. 15 illustrates the catheter assembly used in the vessel occlusion system of FIG. 1, wherein the ablation electrode is shown in its collapsed state.

Thus, it can be appreciated longitudinal translation of the catheter member 120 relative to the catheter sheath 110 in a distal direction 132 deploys the ablation electrode 128 out of the axial opening 118 located at the distal end 114 of the catheter sheath 110 (as shown in FIG. 1), and longitudinal translation of the catheter member 120 relative to the catheter sheath 110 in a proximal direction 134 retracts the ablation electrode 128 into the axial opening 118 (as shown in FIG. 15).

Figure 2:
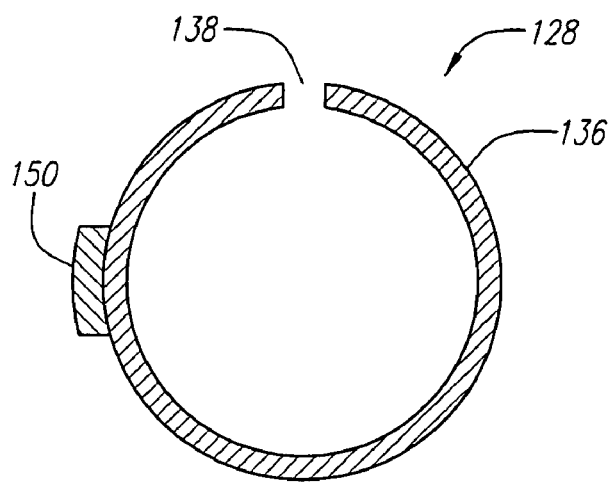
FIG. 2 illustrates a cross-sectional view of an ablation electrode used in the catheter assembly of FIG. 1, wherein the ablation electrode is particularly shown in its expanded state.
Figure 3:
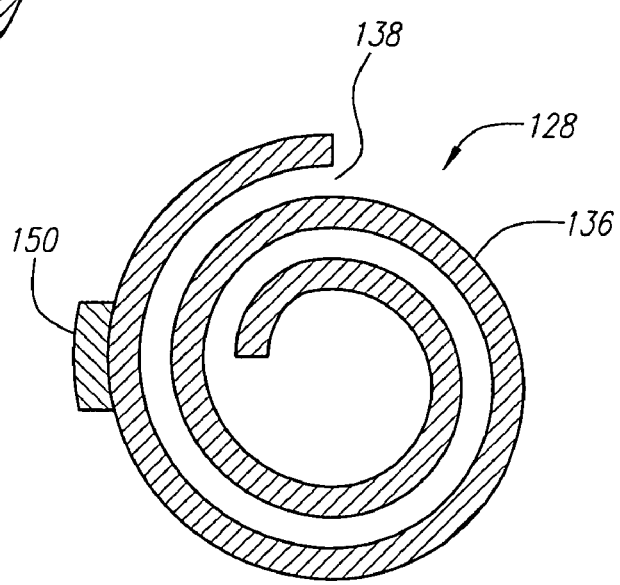
FIG. 3 illustrates a cross-sectional view of the ablation electrode of FIG. 2 in its collapsed state.

The RF ablation electrode 128 comprises a conically shaped wall 136 that is composed of a suitably electrically conductive and resilient material, such as, e.g., stainless steel. The RF ablation electrode 128 further comprises an axial slit 138 (shown in FIGS. 2 and 3) formed within the conical wall 136, such that the wall 136 of the RF ablation electrode 128 is capable of sliding within itself. Due to the resilient and sliding nature of the conical wall 136, the RF ablation electrode 128 will collapse inward in the presence of a compressive force (FIG. 3), e.g., when the vessel segment collapses onto the ablation electrode 128, and expand outward when the compressive force is removed (FIG. 2), e.g., when the ablation electrode 128 is moved away from the collapsed vessel segment to an open vessel segment.

The catheter assembly 102 further comprises a connector assembly 140, which includes a connector sleeve 142 mounted to the proximal end 112 of the catheter sheath 110 and a connector member 144 slidably engaged with the sleeve 142 and mounted to the proximal end 122 of the catheter member 120. The sleeve 142 of the connector assembly 140 comprises a fluid port 146 in fluid communication with the central lumen 116. The connector member 144 comprises an electrical connector 148 in which the RF wires 130 and sensor wires (described below) extending through the catheter member 120 are coupled. The connector assembly 140 can be composed of any suitable rigid material, such as, e.g., metal, plastic, or the like.

Lastly, the catheter assembly 102 comprises a temporary compression sleeve 115 that is slidably disposed over the ablation electrode 128, so that the ablation electrode 128 is maintained in a completely collapsed state when located within the distal end 114 of the catheter sheath 112. This facilitates the deployment of the ablation electrode 128 by preventing the dynamic sealing member 166 (described below) from interfering with the distal motion of the ablation electrode 114 prior to its deployment. Specifically, as the collapsed ablation electrode 114 is distally translated with the temporary compression sleeve 115, the temporary compression sleeve 115 abuts the dynamic sealing member 166. As a result, the distal movement of the temporary compression sleeve 115 is ceased, while distal movement of the retracted ablation electrode 128, which is spaced towards the center of the catheter sheath 110 by the temporary compression sleeve 115, bypasses the dynamic sealing member 166 and continues out through the distal end 114 of the catheter sheath 110.

The sensor assembly 104 includes a sensor 150 associated with the RF ablation electrode 128, external sensing circuitry 152 associated with the automated longitudinal translator 108, and sensor wires 154 that extend from the sensor 150 back through the wire lumen 126 of the catheter member 120 to the sensing circuitry 152. Alternatively, a telemetry device (not shown) can be implanted within the catheter member 120, so that the sensing circuitry 152 can remotely and wirelessly communicate with the sensor 150. In the illustrated embodiment, the sensor 150 takes the form of a piezo-resistive type strain gage, which are standard in the art. One such example is a metal-foil strain gage, a commercial embodiment of which is marketed by Omega Engineering, Inc., located in Stamford, Conn. Other types of strain gages can be used as well. For example, laser fiber-based strain gages, such as those manufactured by EGNG IC Sensors, Inc., located in Milpitas, Calif., or Micro Electro-Mechanical Systems (MEMS)-based strain gages, such as those manufactured by CardioMems, Inc., located in Atlanta, Ga., can be used for the sensor 150.

As shown in the illustrated embodiment, the sensor 150 is suitably bonded to the outer surface of the conical wall 136. Alternatively, the sensor 150 can be suitably bonded to the inner surface of the conical wall 136. Even more alternatively, multiple sensors 150 can be bonded to the inner and/or outer surfaces of the conical wall 136 to effectively multiply the sensor assembly's 104 sensitivity, since the sensor 150 on the inner surface of the conical wall 136 will be loaded in compression, and the sensor 150 on the outer surface of the conical wall 136 will be loaded in tension when the ablation electrode 128 is compressed. In any event, it will be appreciated that as the RF ablation electrode 128 collapses and expands, thereby varying the curvature of the conical wall 136, the strain induced on the sensor 150 will vary, which in turn varies the resistance of the sensor 150.

Figure 4:
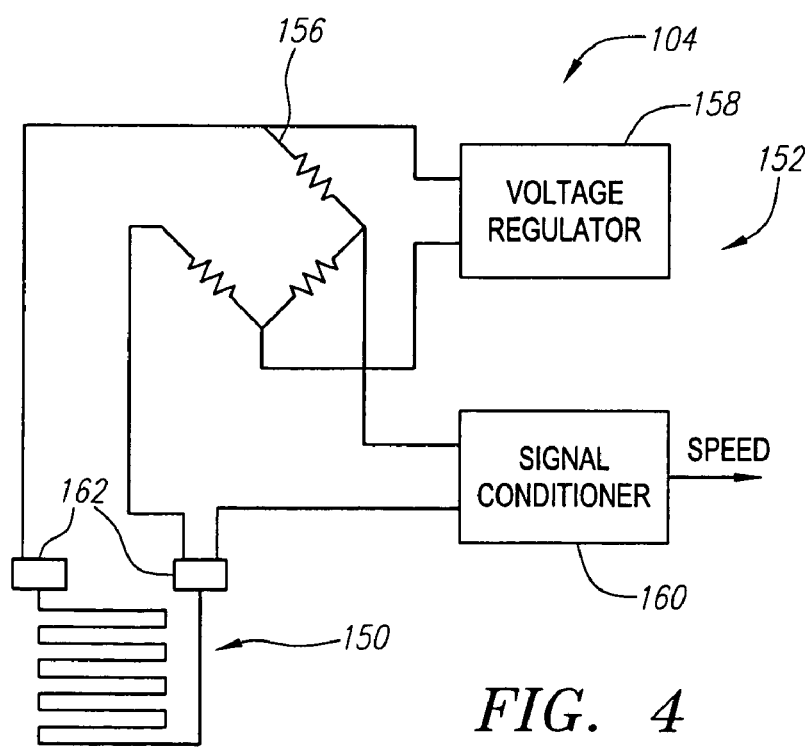
FIG. 4 is a schematic diagram of external sensing circuitry used in the vessel occlusion system of FIG. 1.

As illustrated in FIG. 4, the external sensing circuitry 152 comprises a wheatstone bridge 156 that is electrically coupled to opposite terminals 162 of the sensor 150, a regulated voltage or current source 158 for exciting the wheatstone bridge 156, and a signal conditioner 160 for monitoring the wheatstone bridge 156. A change in resistance of the sensor 150 will produce an imbalance in the bridge 156, which is sensed by the signal conditioner 160. Further details concerning the sensor 150 and sensing circuitry 152 are disclosed in U.S. Pat. No. 5,083,573, entitled "Method of and Means for Implanting a Pressure and Force Sensing Apparatus," which is hereby fully and expressly incorporated herein by reference.

Accordingly, the signals generated by the sensor assembly 104 are indicative of the extent to which the ablation electrode 128 has collapsed or expanded, which in turn, is indicative of the state of closure of a vessel 170 (illustrated in FIG. 5) that bears against the conical wall 136 of the ablation electrode 128. As will be described in further detail below, these signals serve as feedback signals $S_{FEED}$ that are used by the automated longitudinal translator 108 to control the longitudinal translation of the ablation electrode 128.

Referring back to FIG. 1, the RF generator 106 is electrically connected to the electrical connector 148 of the connector assembly 140, which as previously described, is electrically coupled to the ablation electrode 128 through the RF wires 130. In the illustrated embodiment, the RF current is delivered to the ablation electrode 128 in a monopolar fashion, which means that current will pass from the ablation electrode 128, which is configured to concentrate the energy flux in order to have an injurious effect on the surrounding tissue, and a dispersive electrode (not shown), which is located remotely from the ablation electrode 128 and has a sufficiently large area so that the current density is low and non-injurious to surrounding tissue. In the illustrated embodiment, the dispersive electrode may be attached externally to the patient, e.g., using a contact pad placed on the patient's flank.

The RF generator 106 is a conventional RF power supply that operates at a frequency in the range from 200 kHz to 1.25 MHz, with a conventional sinusoidal or non-sinusoidal wave form. Such power supplies are available from many commercial suppliers, such as Valleylab, Aspen, and Bovie. Most general purpose electrosurgical power supplies, however, operate at higher voltages and powers than would normally be necessary or suitable for vessel occlusion. Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 50 W to 200 W, and will usually having a sine wave form, although other wave forms would also be acceptable. The current provided will usually be in the range from 50 mA to 1 A, with the actual magnitude of the current depending primarily on vessel size, i.e., larger vessels will usually require higher currents. Power supplies capable of operating within these ranges are available from commercial vendors, such as RadioTherapeutics of Mountain View, Calif., which markets these power supplies under the trademarks RF2000™ (100 W) and RF3000™ (200 W).

In the illustrated embodiment, the automated longitudinal translator 108 hydromechanically provides for reciprocal longitudinal movement of the catheter member 120, and thus the ablation electrode 128, relative to the catheter sheath 110. To this end, the longitudinal translator 108 comprises a pump 162, which is coupled to the fluid port 146 on the connector assembly 140, and a controller 164, which operates the pump 162 to provide a controlled pressure within the catheter sheath 110 relative to a stable set point. Thus, the pump 162 can be controlled to alternately reduce the pressure within the catheter sheath 110, thereby translating the catheter member 120 relative to the catheter sheath 110 in the proximal direction 134, and increase the pressure within the catheter sheath 110, thereby translating the catheter member 120 relative to the catheter sheath 110 in the distal direction 132. To facilitate this, the catheter member 120 and catheter sheath 110 are placed in a sealing arrangement by providing a dynamic sealing member 166 between the distal ends 114 and 124 of the catheter sheath 110 and catheter member 120, and a dynamic sealing member 168 between the proximal end 122 of the catheter member 120 and the connector sleeve 142 of the connector assembly 140. A commercial embodiment of a pump system that can be used in the automated longitudinal translator 108 is marketed as the Model 8004 RF generator and Pump System by Cardiac Pathways, Inc., located in San Jose, Calif. In this commercial embodiment, the pump system was originally designed to pump saline through a RF catheter to cool the tissue to be ablated, but can be modified to induce "positive" or "negative" pressure within the catheter sheath 110 to translate the catheter member 120 based on the feedback signals $S_{FEED}$ generated by the sensor assembly 104. The RF generator embodied in the Model 8004 system can also be conveniently used for the RF generator 106.

In alternative embodiments, the automated longitudinal translator 108 can provide reciprocal longitudinal movement of the catheter member 120 and ablation electrode 128 relative to the catheter sheath 110 using other means, such as, e.g., a motor and pulley, or drive screw system that reciprocally moves a drive pin directly coupled to the catheter member 120.

The sensor assembly 104 is electrically coupled to the controller 164 of the automated longitudinal translator 108, so that the controller 164 can determine when to initiate and cease longitudinally translation of the catheter member 120. That is, the sensor assembly 104 will provide feedback signals $S_{FEED}$ to the automated longitudinal translator 108 indicative of the extent to which the relevant segment of the vessel is closed or open. As will be described in further detail below, the automated longitudinal translator 108 is configured to proximally translate the catheter member 120, and thus the ablation electrode 128, relative to the catheter sheath 110, when the feedback signal $S_{FEED}$ from the sensor assembly 104 indicates that the relevant segment of the vessel has been closed and occluded, and is configured to cease proximal translation of the catheter member 120, and thus the ablation electrode 128, relative to the catheter sheath 110 when the feedback signal $S_{FEED}$ from the sensor assembly 104 indicates that a relevant vessel segment is open and not occluded.

It should be noted that the catheter assembly 102 can use other types of RF ablation electrodes besides the conically shaped RF electrode 128. For example, FIGS. 13 and 14 shows a pair of opposing RF ablation electrode arms 188 that are composed of a suitably electrically conductive and resilient material, such as, e.g., stainless steel. Due to their resilient nature, the ablation arms 188 will collapse inward in the presence of a compressive force (FIG. 14), e.g., when the vessel segment collapses onto the ablation arms 128, and expand outward when the compressive force is removed (FIG. 13), e.g., when the ablation arms 188 are moved away from the collapsed vessel segment to an open vessel segment. As illustrated, each of the ablation arms 188 comprises a,rectilinear segment 190 and a curvilinear segment 192 that everts outward from the rectilinear segment 190. Thus, the curvilinear segment 192 will tend to straighten out when subject to a compressive force and return to its natural curvilinear geometry when the compressive force is removed. As will be described below, the proximal portion 194 of the curvilinear segment 192 advantageously has a relatively high radius of curvature compared to the distal portion 196 of the curvilinear segment 192. The ablation arms 188 can be configured in either a monopolar or a bipolar arrangement.

When the pair of electrode arms 188 is used, the sensor assembly 104 comprises two sensors 150 that are respectively bonded to the arms 188. Thus, it will be appreciated that as the ablation arms 188 collapse and expand, thereby varying the curvature of the arms 188, the strain induced on the sensors 150 will vary, which in turn varies the resistance of the sensors 150. As shown, the sensors 150 are preferably bonded to the proximal portions 194 of the curvilinear segment 192, since the stress applied to these proximal portions 194 will be magnified due to the relatively high curvatures. As a result, the sensors 150 will be more sensitive to a collapsing vessel segment.

Figure 5A:
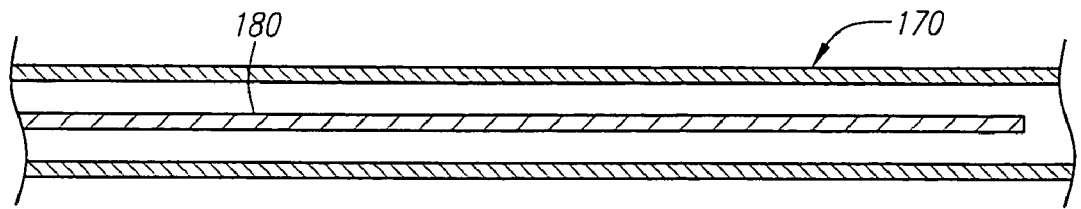
FIGS. 5A–5J illustrates cross-sectional views of one preferred method of using the vessel occlusion system of FIG. 1 to occlude a blood vessel.
Figure 5B:
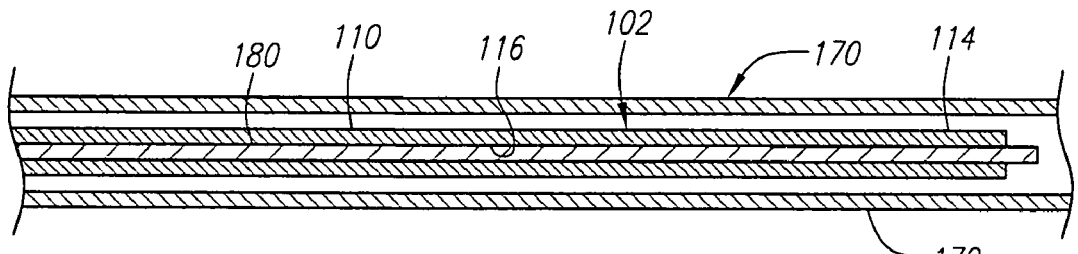
Figure 5C:
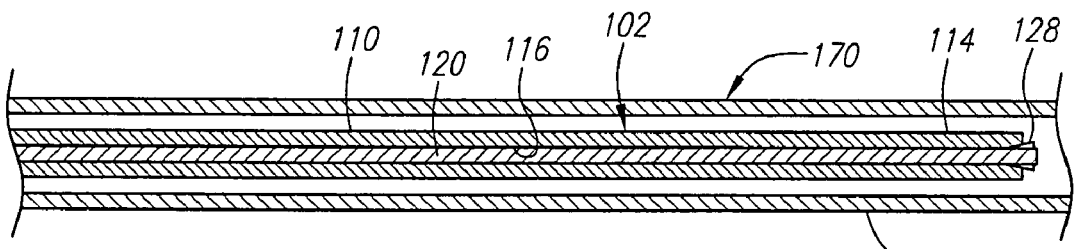
Figure 5D:
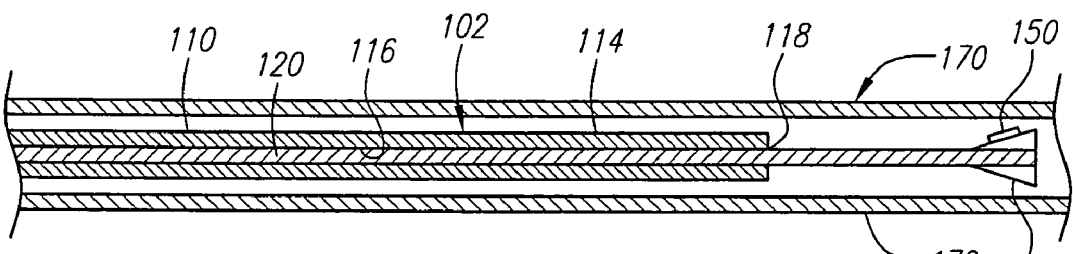
Figure 5E:
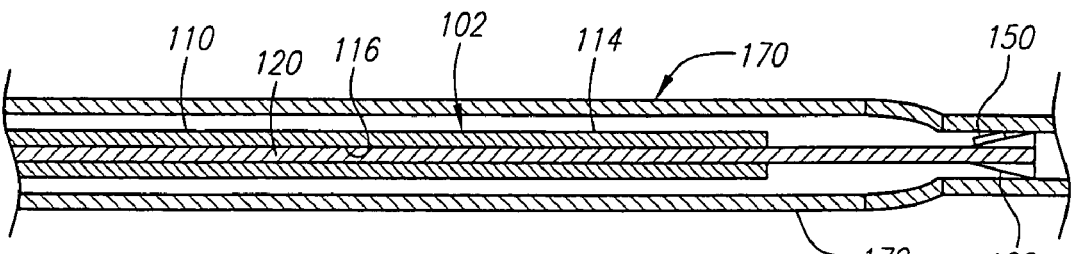
Figure 5F:
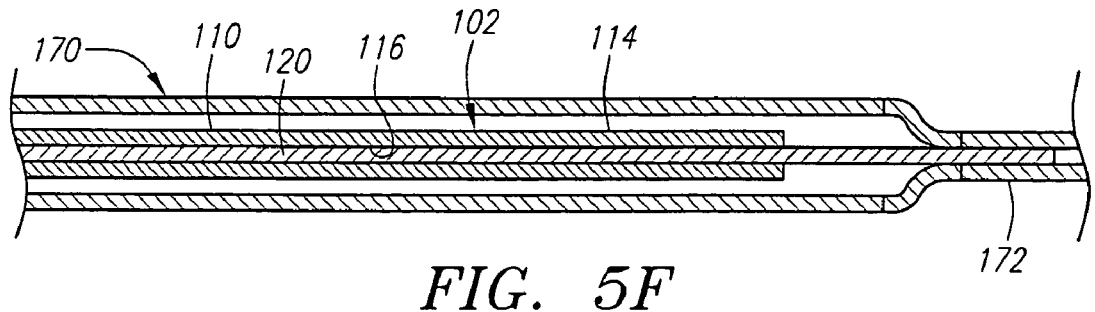
Figure 5G:
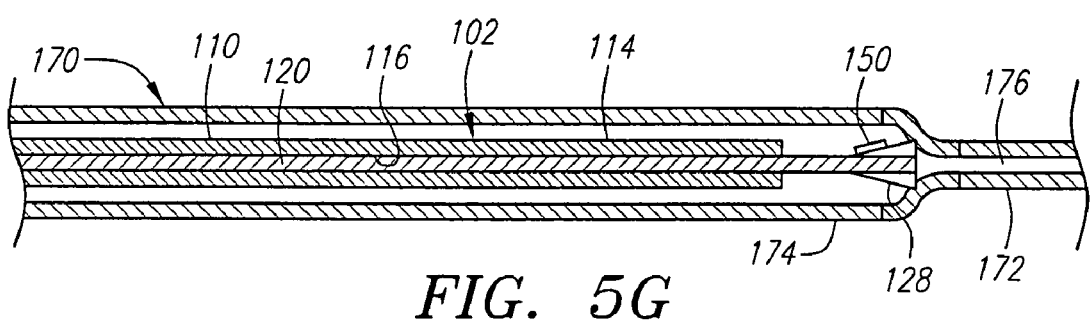
Figure 5H:
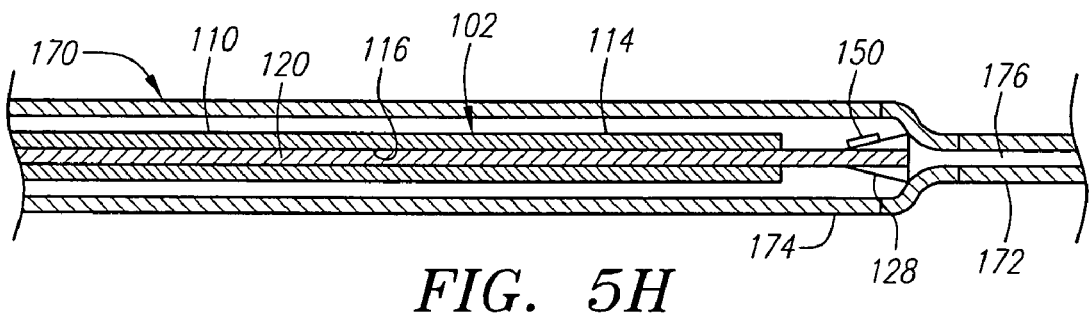
Figure 5I:
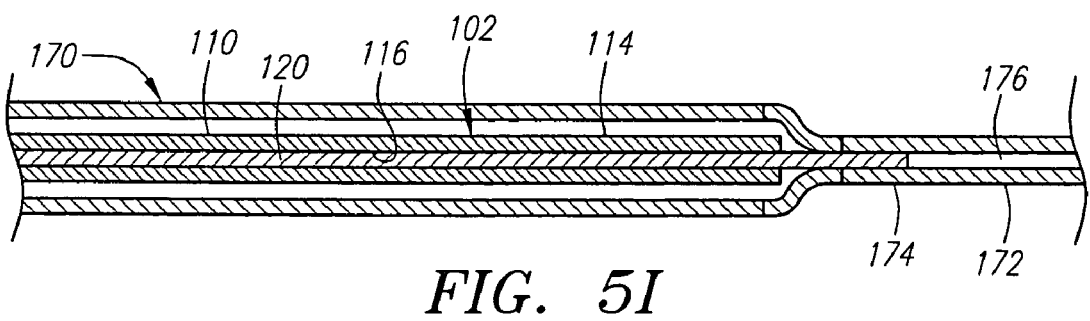

Having described the structure of the vessel occlusion system 100, its operation in occluding a blood vessel 170 will now be described with reference to FIGS. 5A–J. First, the catheter assembly 102 is introduced transluminally through an entry site to a desired target segment 172 of the vessel 170. This can be performed conventionally by introducing a guidewire 180 through the blood vessel 170 (FIG. 5A), and then introducing the catheter sheath 110 (without the catheter member 120) in a conventional "over-the-wire" manner until the distal end 114 of the catheter sheath 110 resides within the target vessel segment 172 (FIG. 5B). The guidewire 180 is then removed from the catheter sheath 110, and then the catheter member 120 is introduced through the central lumen 116 of the catheter sheath 110 until the ablation electrode 128 resides within the distal end 114 of the catheter sheath 110 (FIG. 5C). As the temporary compression sleeve 115 encounters the dynamic sealing member 166 (both not shown), it will slide off of the ablation electrode 128 and remain in the distal end 114 of the catheter sheath 110. While maintaining the connector member 144 in a fixed position, the connector sheath 110 is pulled proximally relative to the catheter member 120, which in turn, removes the remaining portion of the temporary compression sleeve 115 and deploys the ablation electrode 128 out from the axial opening 118 at the distal end 114 of the catheter sheath 110 and into the target vessel segment 172 (FIG. 5D). In order to stabilize the catheter sheath 110 relative to the patient's body, the connector sleeve 142 or otherwise the portion of the catheter sheath 110 residing outside of the blood vessel 170, is sutured, taped, or clamped to the patient just proximal to the entry site. The RF generator 106 and automated longitudinal translator 108 are then coupled to the connector assembly 140, and the sensor assembly 104 is then operated to calibrate the sensor 150. That is, as illustrated in FIG. 6, the magnitude of the feedback signal $S_{FEED}$ that indicates an open vessel state (which defines an open vessel threshold described below), is determined. Once the sensor 150 has been calibrated, the RF generator 106 is then operated to convey RF energy to the ablation electrode 128 to ablate the endothelial wall of the vessel segment 172, which after a period of time, results in the collapsing and occlusion of the vessel segment 172 (FIG. 5E).

As the vessel segment 172 collapses, the ablation electrode 128, in turn, collapses by sliding inward within itself. As a result, the sensor 150 is subjected to an increased strain, as illustrated in FIG. 6. Once the magnitude of the feedback signal $S_{FEED}$ equals a closed vessel threshold $S_{CLOSED}$, indicating a closed vessel state, i.e., the vessel segment 172 is closed or occluded (FIG. 5F), the controller 164 operates the pump 162 to reduce the pressure within the catheter sheath 110, thereby proximally translating the catheter member 120, and thus the ablation electrode 128, away from the closed vessel segment 172 (FIG. 5G). As the ablation electrode 128 is moved away from the closed vessel segment 172 into the next proximal vessel segment 174, which is open, the ablation electrode 128, in turn, expands by sliding outward within itself. As a result, the sensor 150 is subjected to a decreased strain, as illustrated in FIG. 6. Once the magnitude feedback signal $S_{CLOSE}$ equals an open vessel threshold $S_{OPEN}$ (as defined in the calibration step), indicating an open vessel state (i.e., the ablation electrode 128 has moved completely out of the closed vessel segment 172 and into the next proximal vessel segment 174), the controller 164 operates the pump 162 to stabilize the pressure within the catheter sheath 110, thereby ceasing further proximal movement of the ablation electrode 128 (FIG. 5H). It is noted that the vessel segment 172 will be highly thrombosed and totally or mostly occluded when the ablation electrode 128 is withdrawn. A small lumen 176 may remain in the closed vessel segment 172 where the ablation electrode 128 had been deployed. Any such remaining lumen 176, however, will quickly occlude by normal inflammatory and clotting processes, thus assuring the closure of the vessel segment 172.

Figure 5J:
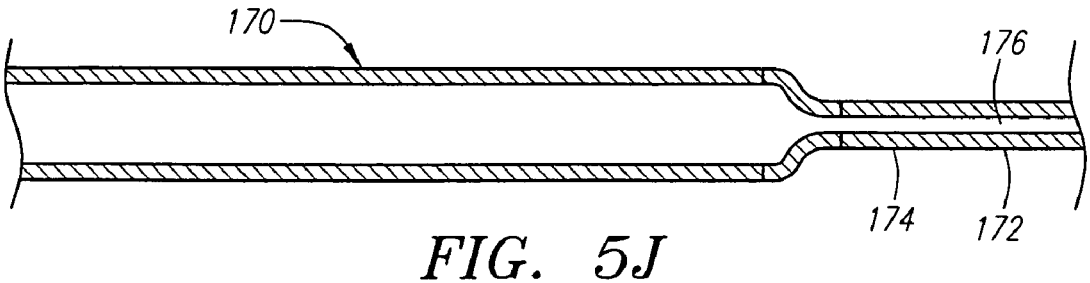
Figure 6:
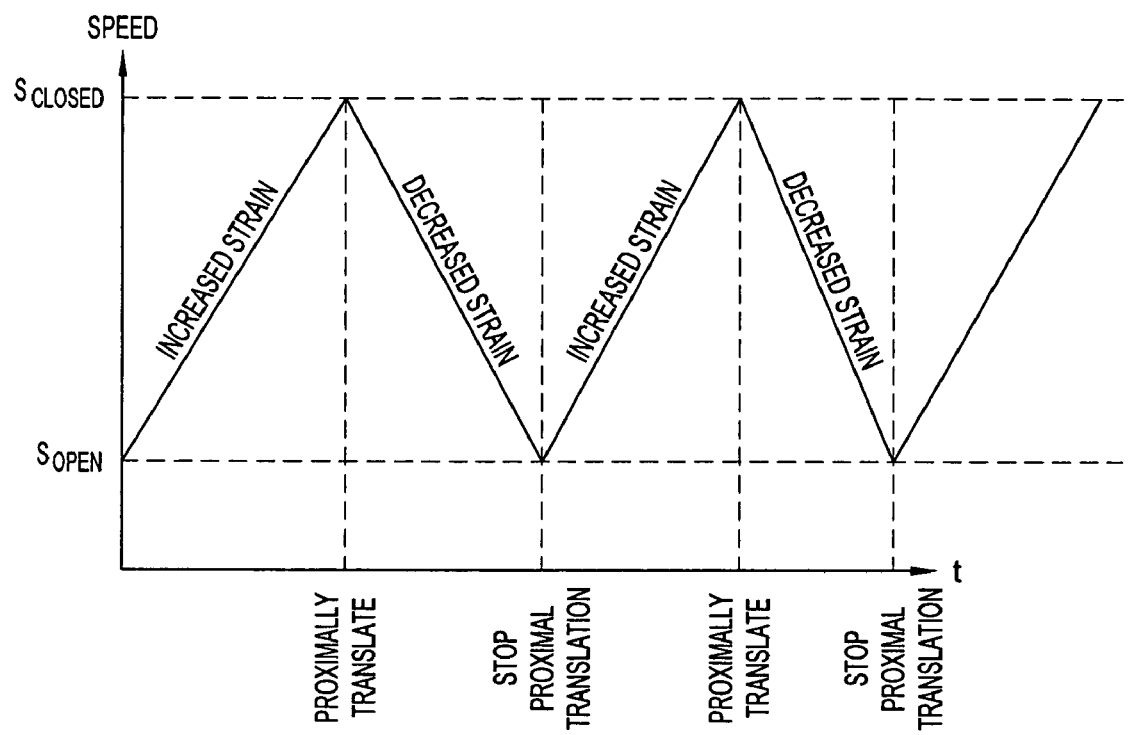
FIG. 6 is a diagram plotting the magnitude of a feedback signal $S_{FEED}$ generated by a sensor assembly of the vessel occlusion system of FIG. 1 over time t.

The process is repeated to occlude the next proximal vessel segment 176, and optionally more proximal segments, thereby forming a longitudinal occlusion 178 (FIG. 5I), and then the catheter assembly 102 is completely removed from the blood vessel 170 (FIG. 5J). Alternatively, the catheter assembly 102 is removed from the blood vessel 170 after the first vessel segment 172 has been occluded, thereby forming an acute point occlusion.

Figure 7:
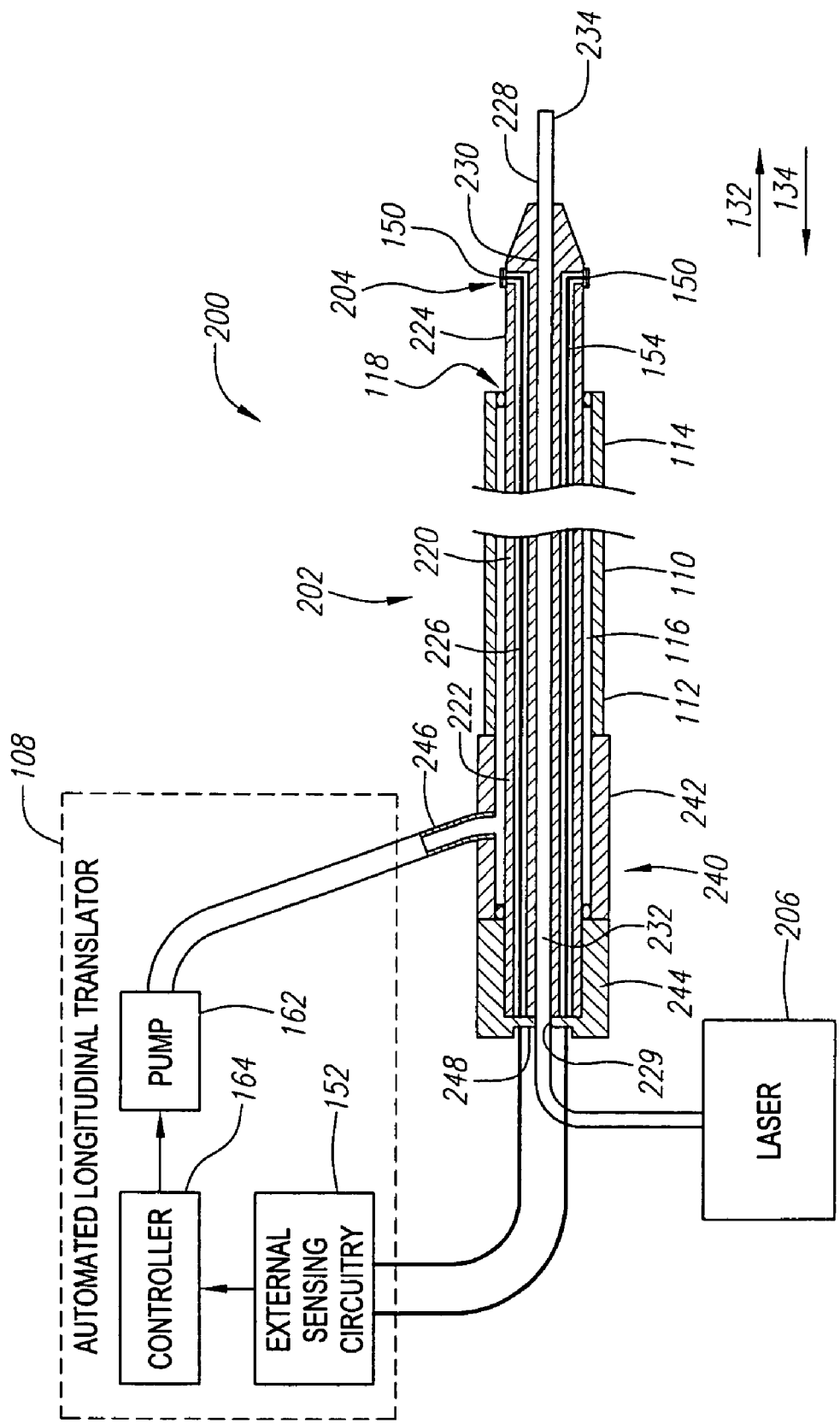
FIG. 7 illustrates a vessel occlusion system constructed in accordance with another preferred embodiment of the present inventions, wherein a catheter assembly used with the vessel occlusion system is particularly shown in cross-section.

FIG. 7 illustrates a vessel occlusion system 200 constructed in accordance with another preferred embodiment of the present inventions. The vessel occlusion system 200 differs from the previously described vessel occlusion system 100 in that it uses laser energy, instead of RF energy, to ablate the endothelial wall of the vessel, and includes one or more sensors that are associated with a catheter member, instead of the ablation device. Specifically, the vessel occlusion system 200 generally comprises a vessel occlusion catheter assembly 202, the sensor assembly 204, a laser 206, and the previously described automated longitudinal translator 108.

The catheter assembly 202 generally comprises the previously described elongated catheter sheath 110 and an elongated catheter member 220 having a proximal end 222, a distal end 224, and a central lumen 230 and wire lumens 226 extending through the catheter member 220 between the proximal and distal ends 222 and 224. The catheter member 220 is slidably disposed within the central lumen 116 of the catheter sheath 110. The catheter assembly 202 further comprises a laser fiber 228 mounted within the central lumen 230 of the catheter member 220. The laser fiber 228 comprises a proximal end 232, and a distal end 234 from which the ablative energy is emitted. The laser fiber 228 is composed of a suitable laser material, such as quartz or optical plastics. The distal end 234 of the laser fiber 228 can be variously configured to provide ablation energy to the tissue. For example, the distal end 234 of the laser fiber 228 can be coated with a suitable heat dispersive substance, e.g., sapphire, such that when laser energy is configured to the distal end 234, it heats up, thereby ablating the tissue in which it contacts. Alternatively, a prism assembly (not shown) can be incorporated onto the distal end 234 of the laser fiber 228, such that laser energy emitted from the distal end 234 is dispersed at an angle, e.g., 30°–90° to the axis of the laser fiber 228.

Thus, it can be appreciated that longitudinal translation of the catheter member 220 relative to the catheter sheath 110 in the distal direction 132 deploys the distal end 234 of the laser fiber 228 out from the axial opening 118 located at the distal end 114 of the catheter sheath 110, and longitudinal translation of the catheter member 220 relative to the catheter sheath 110 in the proximal direction 134 retracts the distal end 234 of the laser fiber 228 into the axial opening 118.

The catheter assembly 202 further comprises a connector assembly 240, which includes a connector sleeve 242 mounted to the proximal end 112 of the catheter sheath 110 and a connector member 244 slidably engaged with the sleeve 242 and mounted to the proximal end 222 of the catheter member 220. The sleeve 242 of the connector assembly 240 comprises a fluid port 246 in fluid communication with the central lumen 116 of the catheter sheath 110. The connector member 244 comprises a connector interface 248 that serves as an electrical connector to which sensor wires (described below) and a locking device for affixing the laser fiber 228 within the catheter member 220. In the illustrated embodiment, the connector interface 248 comprises an aperture 229 through which the laser fiber 228 extends in an interference type arrangement, e.g., a frictional fit or detent mechanism. The connector assembly 240 can be composed of the same material as the previously described connector.

Optionally, rather than using a separate catheter sheath 110, the catheter member 220 can be configured as a sheath in which the laser fiber 228 is slidably disposed. In this case, the connector sleeve 242 will be mounted to the proximal end 222 of the catheter member 220, and the connector member 244 will secure the laser fiber 228.

In any event, the laser 206 is optically connected to the proximal end 232 of the laser fiber 228. The laser 206 provides laser energy at a suitable wavelength, e.g., 810 nm, and at a suitable power, e.g., 15–60 W. A commercial embodiment of vessel occlusion system that includes the basic form of the catheter assembly and laser is manufactured by Diomed, Inc., located in Andover, Mass., and marketed as the ELVT™ system.

The sensor assembly 204 includes a plurality of the previously described sensors 150 associated with the distal end 224 of the catheter member 220. The sensor assembly 204 further includes the previously described external sensing circuitry 152 (shown in FIG. 4) associated with the automated longitudinal translator 108, and sensor wires 154 that extend from the sensors 150 back through the wire lumens 226, which are formed through the catheter member 120 to the sensing circuitry 152. As can be appreciated, as the distal end 224 of the catheter member 220 collapses and expands, the strain induced on the sensors 150 will vary, which in turn varies the resistance of the sensors 150.

As previously described, a change in resistance of the sensors 150 will produce an imbalance in the bridge 156, which is sensed by the signal conditioner 160, and accordingly, the feedback signals $S_{FEED}$ generated by the sensor assembly 204 are indicative of the extent to which the distal end 224 of the catheter member 220 has collapsed or expanded, which in turn, is indicative of the extent to which a vessel that bears against the laser fiber 228 is closed or opened.

Alternatively, instead of using strain gages, temperature sensors, such as, e.g., thermistors or thermocouples. In this case, the temperature sensors can sense the collapsing of a vessel by measuring temperature, as will be described in further detail below. For example, a measured temperature of 70° C. or more may indicate that the ablated vessel is closed. Even more alternatively, other types of sensors, such as impedance sensors or ultrasound echoing transducers, can be used to sense the collapsing of a vessel.

The automated longitudinal translator 108 alternately provides "negative" and "positive" pressure within the catheter sheath 110, thereby providing reciprocal longitudinal movement of the catheter member 220, and thus the distal end 234 of the laser fiber 228, relative to the catheter sheath 110. Alternatively, the automated longitudinal translator 108 using other suitable means, such as a motor and pulley or drive screw system that reciprocally moves the catheter member 220. The sensor assembly 204 is electrically coupled to the controller 164 of the automated longitudinal translator 108, so that the controller 164 can determine when to initiate and cease longitudinally translation of the catheter member 220, as previously described.

Figure 8A:
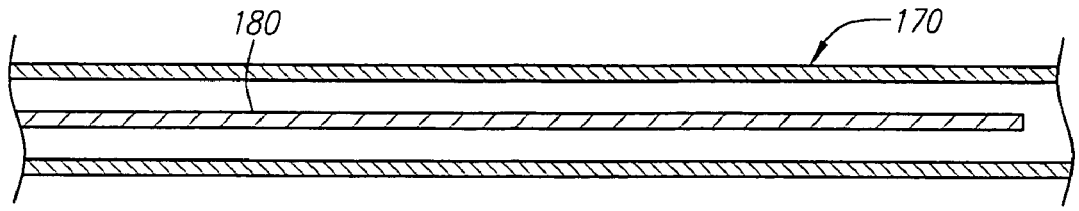
FIGS. 8A–8J illustrates cross-sectional views of one preferred method of using the vessel occlusion system of FIG. 7 to occlude a blood vessel.
Figure 8B:
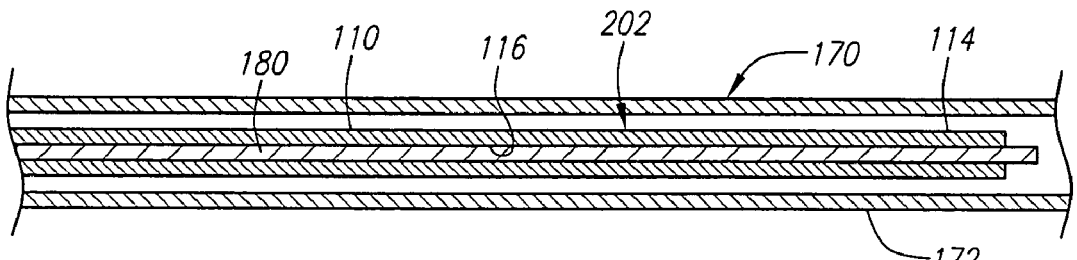
Figure 8C:
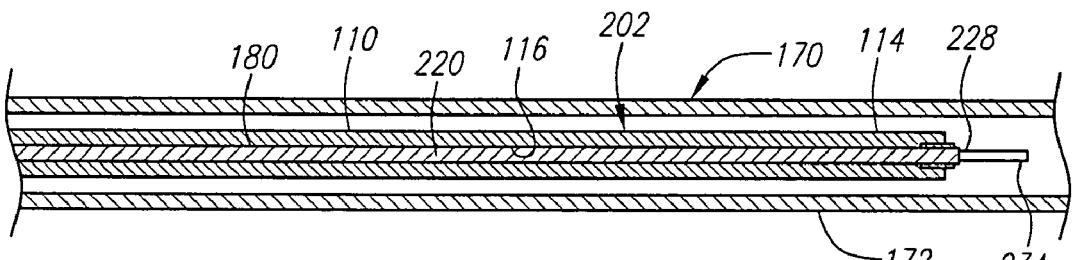
Figure 8D:
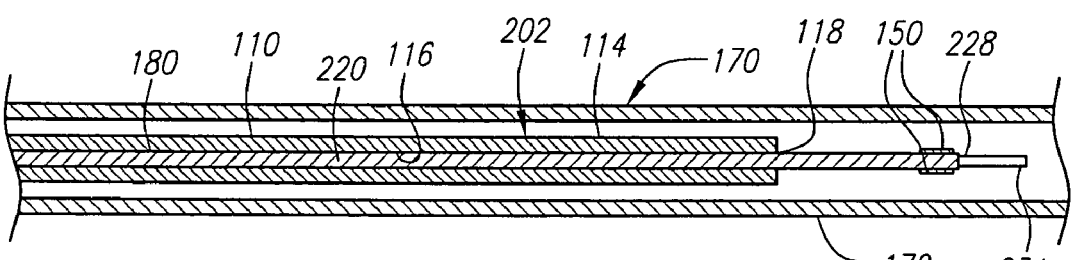
Figure 8E:
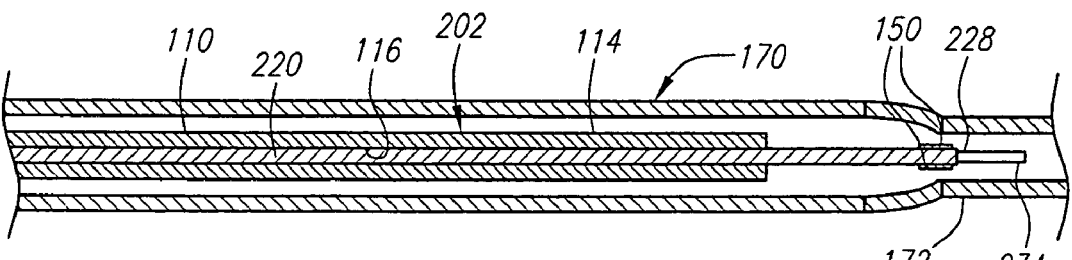
Figure 8F:
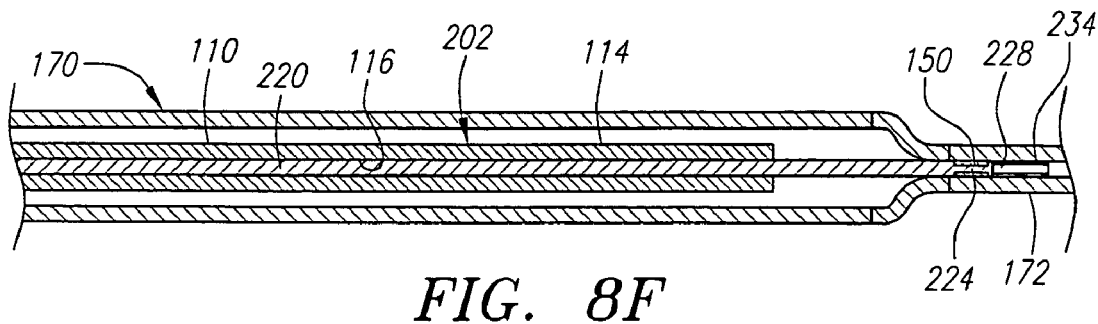

Having described the structure of the vessel occlusion system 200, its operation in occluding the blood vessel 170 will now be described with reference to FIGS. 8A–J. First, the catheter assembly 202 is introduced transluminally through an entry site to a desired target segment 172 of the vessel 170. This can be performed conventionally by introducing a guidewire 180 through the blood vessel 170 (FIG. 8A), and then introducing the catheter sheath 110 (without the laser fiber 228) in a conventional "over-the-wire" manner until the distal end 114 of the catheter sheath 110 resides within the target vessel segment 172 (FIG. 8B). The guidewire 180 is then removed from the catheter sheath 110, and then the catheter member 220 with the laser fiber 228 is introduced through the central lumen 116 of the catheter sheath 110 until the distal end 234 of the laser fiber 228 resides within the distal end 114 of the catheter sheath 110 (FIG. 8C). While maintaining the connector member 244 in a fixed position, the connector sheath 110 is pulled proximally relative to the catheter member 220, which in turn, deploys the distal end 234 of the laser fiber 228 out from the axial opening 118 at the distal end 114 of the catheter sheath 110 and into the target vessel segment 172 (FIG. 8D). In order to stabilize the catheter sheath 110 relative to the patient's body, the connector sleeve 242 or otherwise the portion of the catheter sheath 110 residing outside of the blood vessel 170, is sutured, taped, or clamped to the patient just proximal to the entry site. The laser 206 and automated longitudinal translator 108 are then coupled to the connector assembly 240, and the sensor assembly 204 is then operated to calibrate the sensors 150. Once the sensors 150 have been calibrated, the laser 206 is then operated to convey laser energy to the distal end 234 of the laser fiber 228 to ablate the endothelial wall of the vessel segment 172, which after a period of time, results in the collapsing and occlusion of the vessel segment 172 (FIG. 8E).

Figure 8G:
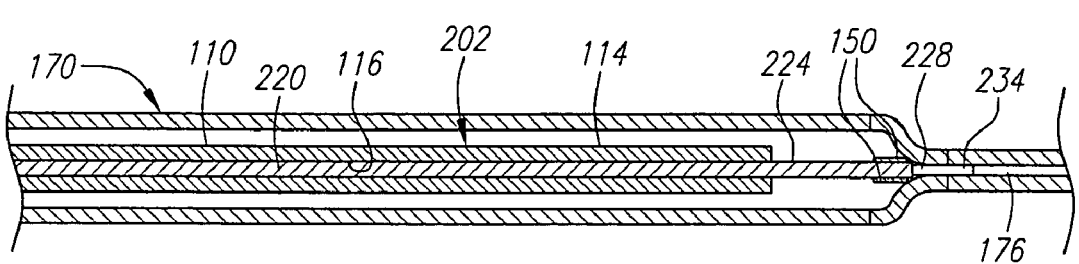
Figure 8H:
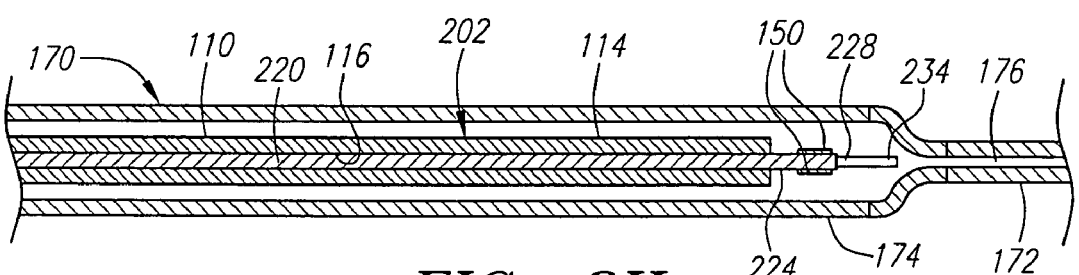
Figure 8I:
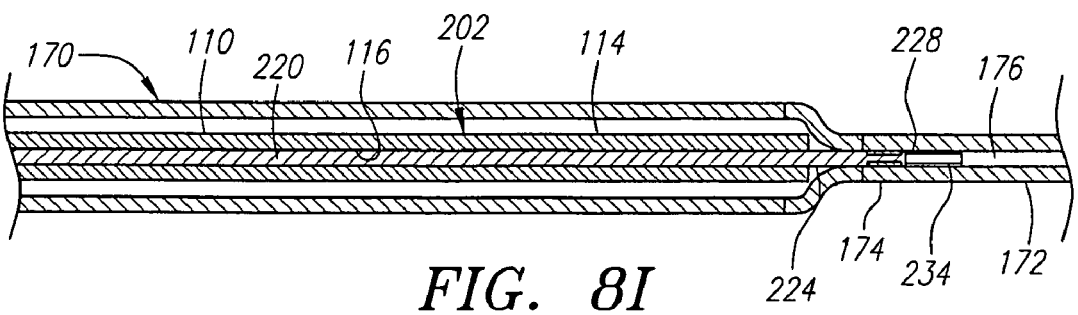

As the vessel segment 172 collapses, the distal end 224 of the catheter member 220 distorts inward. As a result, the sensors 150 are subjected to an increased strain, as illustrated in FIG. 6. Alternatively, if the sensors 150 are temperature or impedance sensors, a measured temperature will exceed a predetermined temperature or impedance threshold. Or if the sensors 150 are ultrasound echoing transducers, the nature of the return acoustic pulses may change. In any case, once the magnitude of the feedback signal $S_{FEED}$ exceeds a closed vessel threshold $S_{CLOSED}$, indicating that the vessel segment 172 is closed or occluded (FIG. 8F), the controller 164 operates the pump 162 to reduce the pressure within the catheter sleeve 242, thereby proximally translating the distal end 224 of the catheter member 220, and thus the distal end 234 of the laser fiber 228, away from the closed vessel segment 172 (FIG. 8G). As the distal end 224 of the catheter member 220 is moved away from the closed vessel segment 172 into the next proximal vessel segment 174, which is open, it distorts outward. As a result, the sensors 150 are subjected to a decreased strain, as illustrated in FIG. 6. Once the magnitude feedback signal $S_{CLOSE}$ drops below the open vessel threshold $S_{OPEN}$ (as defined in the calibration step) indicating that the distal end 234 of the laser fiber 228 has move completely out of the closed vessel segment 172 and into the next proximal vessel segment 174, the controller 164 operates the pump 162 to stabilize the pressure within the catheter sleeve 242, thereby ceasing further proximal movement of the catheter member 220 (FIG. 8H). It is noted that the vessel segment 172 will be highly thrombosed and totally or mostly occluded when the distal end 234 of the laser fiber 228 is withdrawn. A small lumen 176 may remain in the closed vessel segment 172 where the distal end 234 of the laser fiber 228 had been deployed. Any such remaining lumen 176, however, will quickly occlude by normal inflammatory and clotting processes, thus assuring the closure of the vessel segment 172.

Figure 8J:
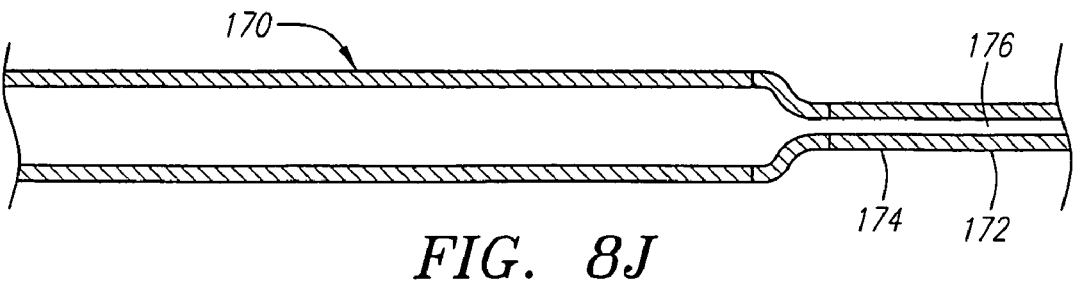

The process is repeated to occlude the next proximal vessel segment 174, and optionally more proximal segments, thereby forming a longitudinal occlusion (FIG. 8I), and then the catheter assembly 202 is completely removed from the blood vessel 170 (FIG. 8J). Alternatively, the catheter assembly 202 is removed from the blood vessel 170 after the first vessel segment 172 has been occluded, thereby forming an acute point occlusion.

Figure 9:
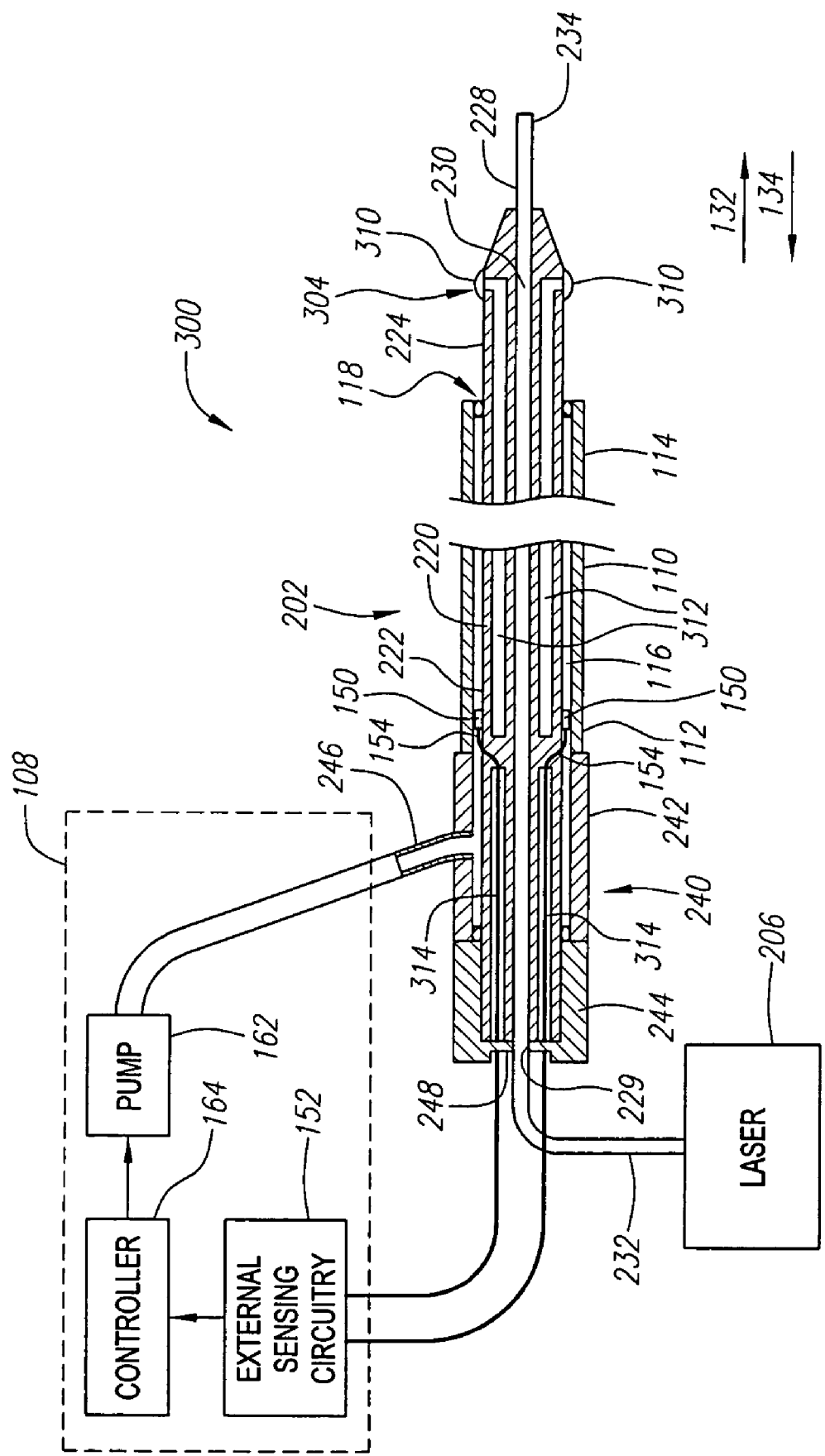
FIG. 9 illustrates a vessel occlusion system constructed in accordance with still another preferred embodiment of the present inventions, wherein a catheter assembly used with the vessel occlusion system is particularly shown in cross-section.

In the previously described embodiments, the sensors of the sensor assembly were located at the distal end of the catheter assembly, either on the ablation element or the distal end of the catheter sheath. The sensors, however, can be located at the proximal end of the catheter assembly or external to the catheter assembly. For example, FIG. 9 illustrates a vessel occlusion system 300 constructed in accordance with still another preferred embodiment of the present inventions. The vessel occlusion system 300 is similar to the previously described vessel occlusion system 200 with the exception that it comprises a sensor assembly 304 that includes proximally located sensors 150. Specifically, the sensor assembly 304 includes a plurality of membranes 310 circumferentially disposed around the distal end 224 of the catheter member 220, an equal plurality of sensors 150 circumferentially disposed around the proximal end 222 of the catheter member 220, and a plurality of lumens 312 that extend between the proximally disposed sensors 150 and the distally disposed membranes 310. The lumens 312 are filled with a suitable liquid, gel, or gas medium. Wire lumens 314 are provided from the sensors 150 back proximally to the connector assembly 240. The sensor wires 154 extend through the wire lumens 314 from the sensors 150 to the connector interface 248.

As can be appreciated, the strain to which the membranes 310 are subjected is transmitted through the medium within the lumens 312 to the sensors 150. That is, as the membranes 310 collapse and expand, the fluid within the lumens 312 are proximally or distally conveyed to expand and collapse the proximal end 222 of the catheter member 220. As a result, the strain induced on the sensors 150 will vary, which in turn varies the resistance of the sensors 150, which is sensed by the external sensing circuitry 152, as previously described. To magnify the transmission of the stress from the distal end 224 of the catheter member 220 to the proximal end 222 of the catheter member 220, the sensors 150 can be optionally located on proximally located membranes that are in fluid communication with the lumens 312.

Figure 10A:
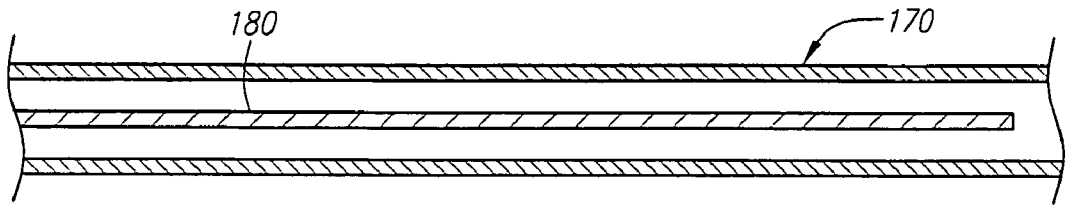
FIGS. 10A–10J illustrates cross-sectional views of one preferred method of using the vessel occlusion system of FIG. 9 to occlude a blood vessel.
Figure 10B:
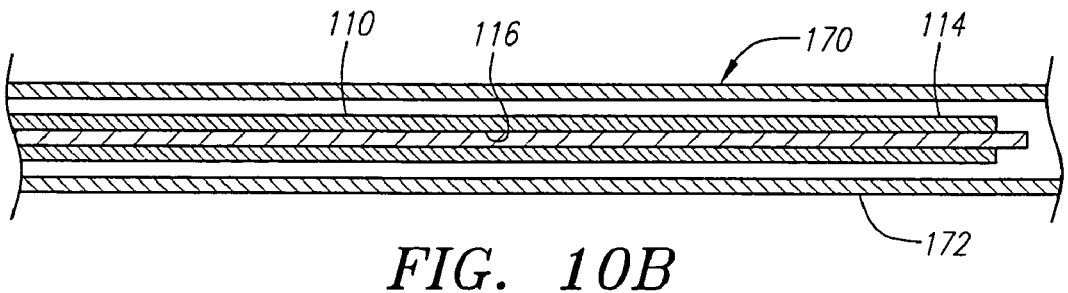
Figure 10C:
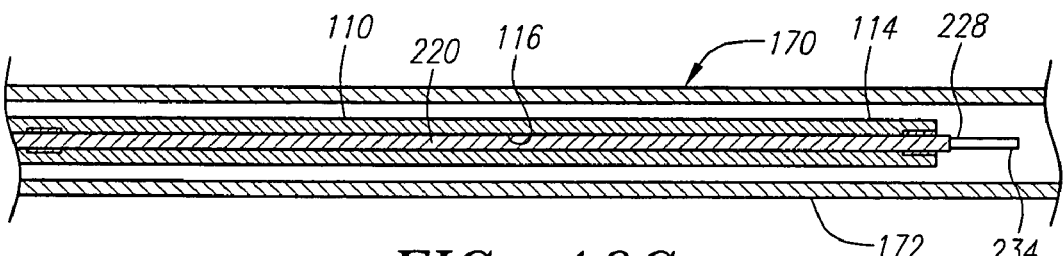
Figure 10D:
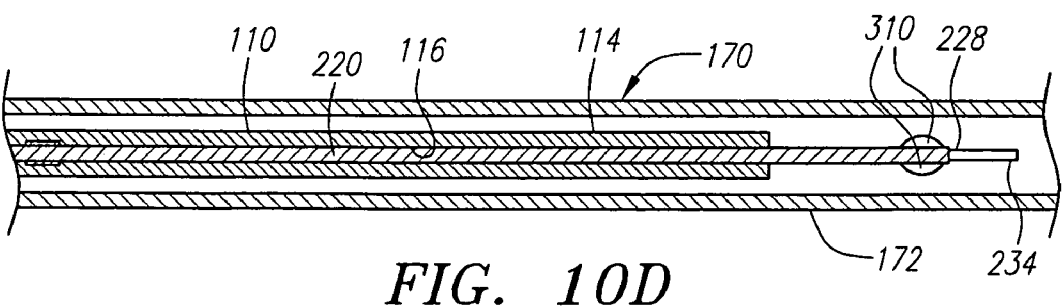
Figure 10E:
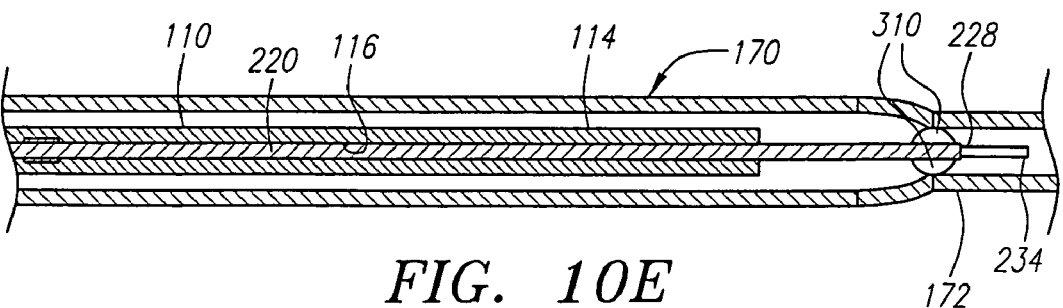
Figure 10F:
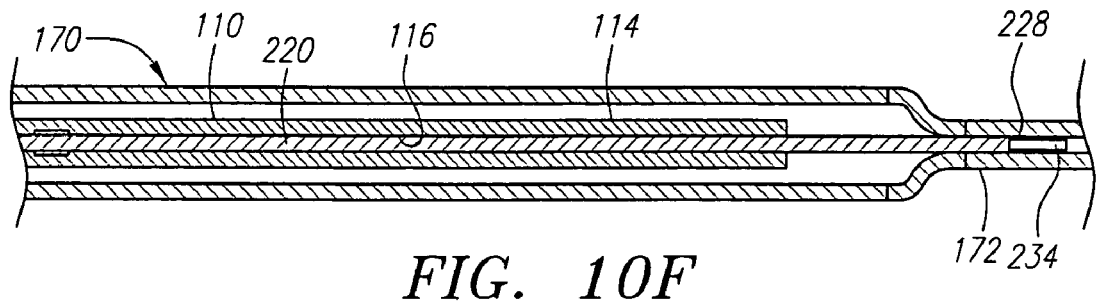
Figure 10G:
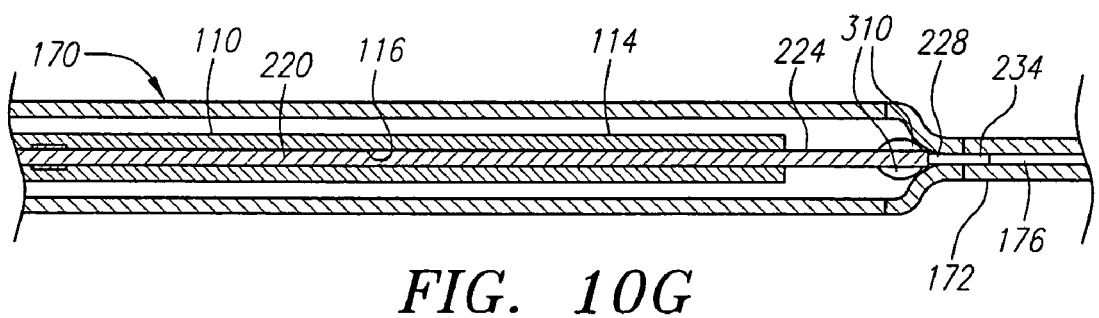

Having described the structure of the vessel occlusion system 300, its operation in occluding the blood vessel 170 will now be described with reference to FIGS. 10A–J. The distal end 234 of the laser fiber 228 is deployed within the desired vessel segment 172, the vessel occlusion system 100 is assembled, and the laser 206 is operated in the same manner as that previously described to collapse and occlude the vessel segment 172 (FIGS. 10A–10E). As the vessel segment 172 collapses, the membranes 310 are compressed. As a result, fluid is proximally conveyed through the lumens 312, thereby expanding the proximal end 222 of the catheter member 220 and subjecting the sensors 150 to an increased strain, as illustrated in FIG. 6. Once the magnitude of the feedback signal $S_{FEED}$ exceeds closed vessel threshold $S_{CLOSED}$, indicating that the vessel segment 172 is closed or occluded (FIG. 10F), the controller 164 operates the pump 162 to reduce the pressure within the catheter sleeve 242, thereby proximally translating the distal end 224 of the catheter member 220, and thus the distal end 234 of the laser fiber 228, away from the closed vessel segment 172 (FIG. 10G). As the distal end 224 of the catheter member 220 is moved away from the closed vessel segment 172 into the next proximal vessel segment 174, which is open, the membranes 310 are no longer compressed. As a result, fluid is distally conveyed from the proximal end 222 of the catheter member 220 through the lumens 312, thereby expanding the membranes 310. As a result, the proximal end 222 of the catheter member 220 contracts, subjecting the sensors 150 to a decreased strain, as illustrated in FIG. 6.

Figure 10H:
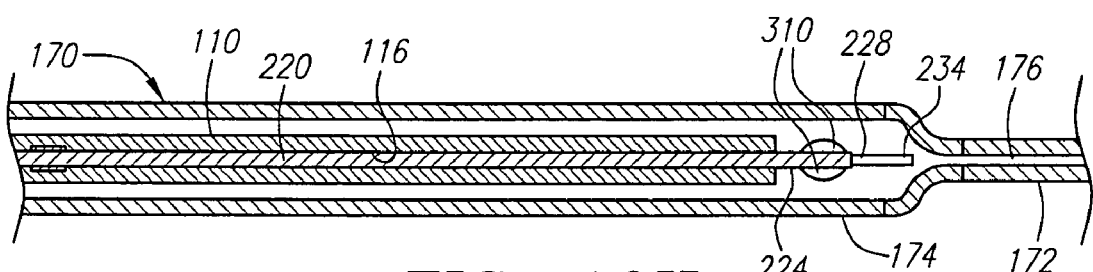
Figure 10I:
Figure 10J:
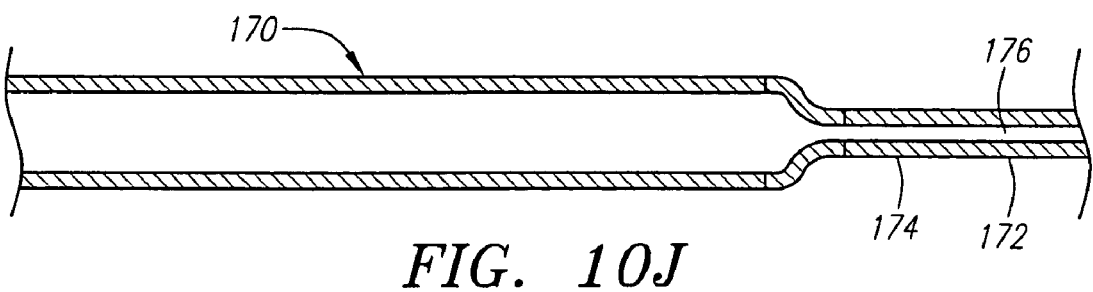

Once the magnitude feedback signal $S_{CLOSE}$ drops below the open vessel threshold $S_{OPEN}$ (as defined in the calibration step) indicating that the distal end 234 of the laser fiber 228 has move completely out of the closed vessel segment 172 and into the next proximal vessel segment 174, the controller 164 operates the pump 162 to stabilize the pressure within the catheter sleeve 242, thereby ceasing further proximal movement of the catheter member 220 (FIG. 10H). The process is repeated to occlude the next proximal vessel segment 174, and optionally more proximal segments, thereby forming a longitudinal occlusion (FIG. 10I), and then the catheter assembly 202 is completely removed from the blood vessel 170 (FIG. 10J). Alternatively, the catheter assembly 202 is removed from the blood vessel 170 after the first vessel segment 172 has been occluded, thereby forming an acute point occlusion.

Figure 11:
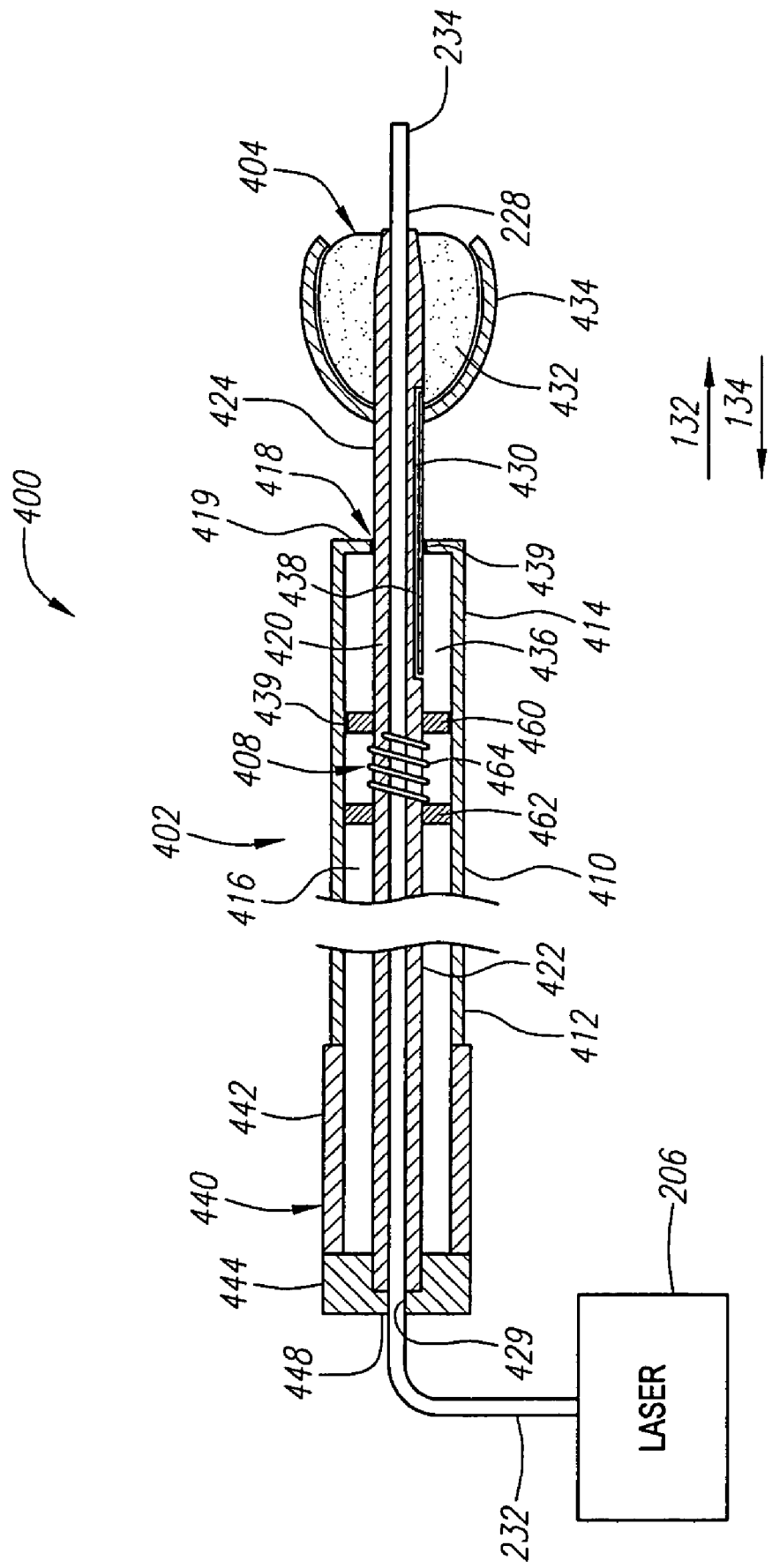
FIG. 11 illustrates a vessel occlusion system constructed in accordance with yet another preferred embodiment of the present inventions, wherein a catheter assembly used with the vessel occlusion system is particularly shown in cross-section.

In the previously described embodiments, the sensor assemblies provided feedback to an external automated longitudinal translator that was, at least partially, electronic in nature. The sensor assemblies, however, can provide feedback to external or internal automated longitudinal translators that is totally mechanical in nature. For example, FIG. 11 illustrates a vessel occlusion system 400 constructed in accordance with another preferred embodiment of the present inventions. The vessel occlusion system 400 generally comprises a vessel occlusion catheter assembly 402, a sensor assembly 404 that provides mechanical feedback, the previously described laser 206, and an automated longitudinal translator 408 that is internal to the catheter assembly 402.

The catheter assembly 402 generally comprises an elongated outer catheter sheath 410 having a proximal end 412, a distal end 414 having an annular flange 419 at its tip, and a central lumen 416 extending through the catheter sheath 410 between the proximal end 412 and an axial port 418 defined by the annular flange 419. The catheter member 420 is slidably disposed within the central lumen 416 of the catheter sheath 410. The catheter assembly 402 further comprises the previously described laser fiber 228 mounted within the central lumen 430 of the catheter member 420. In the illustrated embodiment, the catheter member 420 extends entirely the length of the catheter sheath 410. Alternatively, the catheter member 420 is only disposed in the distal end 414 of the catheter sheath 410.

Thus, it can be appreciated that longitudinal translation of the catheter member 420 relative to the catheter sheath 410 in the distal direction 132 deploys the distal end 234 of the laser fiber 228 out from the axial opening 418 located at the distal end 414 of the catheter sheath 410, and longitudinal translation of the catheter member 420 relative to the catheter sheath 410 in the proximal direction 134 retracts the distal end 234 of the laser fiber 228 into the axial opening 418.

The catheter assembly 402 further comprises a connector assembly 440, which includes a sleeve 442 mounted to the proximal end 412 of the catheter sheath 410 and a connector member 444 slidably engaged with the sleeve 442 and mounted to the proximal end 422 of the catheter member 420. The connector member 444 comprises a locking device 448 for affixing the laser fiber 228 within the catheter member 420. In the illustrated embodiment, the connector interface 448 comprises an aperture 429 through which the laser fiber 228 extends in an interference type arrangement, e.g., a frictional fit or detent mechanism. The connector assembly 440 can be composed of the same material as the previously described connector. The laser 206 is optically connected to the proximal end 232 of the laser fiber 228. In the alternative embodiment where the catheter member 420 only extends the length of the distal end 414 of the catheter sheath 410, the connector assembly 440 comprises a single piece connector that comprises the locking device 448.

The sensor assembly 404 includes an expandable/collapsible balloon 432 mounted to the distal end 424 of the catheter member 420 and a pair of rigid arms 434 that are hingedly attached to the distal end 424 of the catheter member 420, such that the arms 434 transmit compressive forces applied by the vessel wall to the balloon 432. The balloon 432 is filled with a suitable liquid, gel or gas medium. The sensor assembly 404 further comprises an annular cavity 436 formed at the distal end of the central lumen 416 between the distal end 414 of the catheter sheath 410 and the distal end 424 of the catheter member 420. The sensor assembly 404 further comprise a lumen 438 disposed through the distal end 424 of the catheter member 420 in fluid communication between the inside of the balloon 432 and the annular cavity 436. As can be appreciated, as the pair of arms 434 move inward and outward, the balloon 432 collapses and expands, transmitting the fluid between the balloon 432 and the annular cavity 436 via the lumen 438.

The automated longitudinal translator 408 comprises an annular flange 460 mounted to the exterior of the catheter member 420 proximal to the annular cavity 436. As shown, the annular cavity 436 is proximally bound by the annular flange 460 and distally bound by the annular flange 419. The annular cavity 436 is sealed by providing dynamic seals 439 between the annular flange 460 and the interior surface of the catheter sheath 410, and between the annular flange 419 and the outer surface of the catheter member 420. The automated longitudinal translator 408 further comprises an annular stop 462 mounted to the internal surface of the catheter sheath 410, and a spring 464 that is in compression between the annular stop 462 and the annular flange 460. A dynamic seal (not shown) can also be provided between the annular flange 460 and the outer surface of the catheter member 420.

Thus, it can be appreciated that when the pair of arms 434 compresses the balloon 432, thereby conveying the medium from the balloon 432 into the annular cavity 436 via the lumen 438, the annular flange 460, and thus the catheter member 420 and laser fiber 218, are forced to move in the proximal direction 134. In contrast, when the pair of arms 434 do not compress the balloon 432, the spring 466 urges the annular flange 460, and thus the catheter member 420 and laser fiber 218, in the distal direction 132. As a result, the medium is conveyed from the annular cavity 436 back into the balloon 432. It can be appreciated that the pressure exhibited by the medium within the annular cavity 436 serves as a feedback signal $S_{FEED}$ indicative of the extent to which the relevant segment of the vessel 170 is closed or open.

In an alternative embodiment, the rigid arms 434 can be configured to provide a means of ablating the vessel 170 in which they are disposed by coupling the RF generator 206 and one or more RF wires 130 thereto. In this case, the laser fiber 228 can be used as another means for ablating the vessel 170, or alternatively, can be removed altogether, leaving the ablative rigid arms 434 as the sole means for ablation.

Figure 12A:
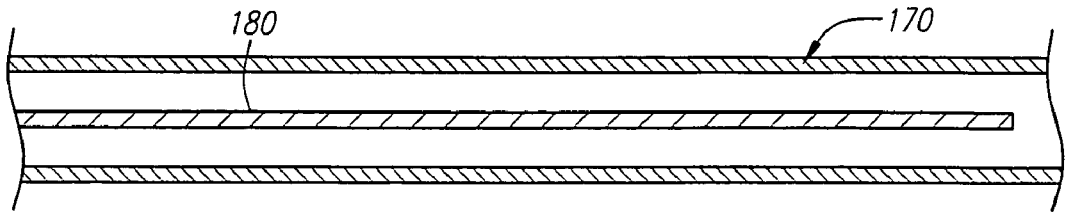
FIGS. 12A–12H illustrates cross-sectional views of one preferred method of using the vessel occlusion system of FIG. 11 to occlude a blood vessel.
Figure 12B:
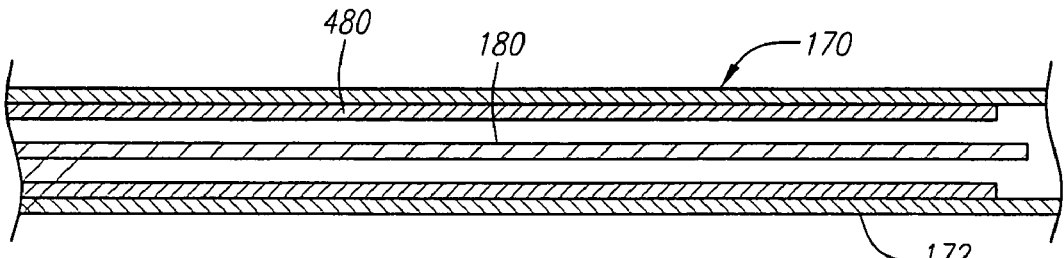
Figure 12C:
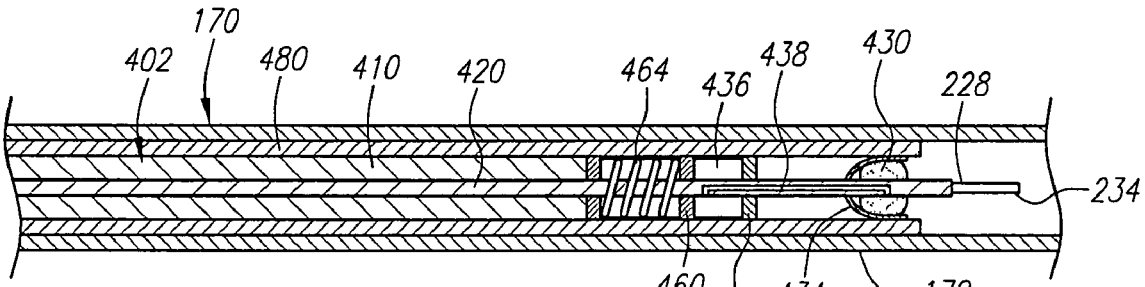
Figure 12D:
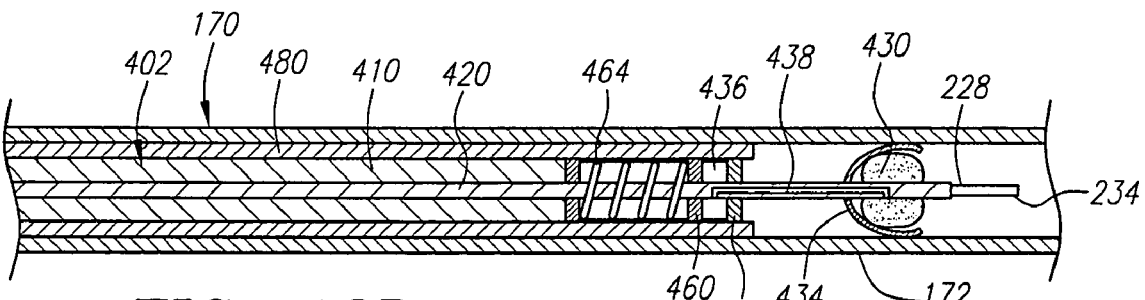

Having described the structure of the vessel occlusion system 400, its operation in occluding the blood vessel 170 will now be described with reference to FIGS. 12A–H. First, the catheter assembly 402 is introduced transluminally through an entry site to the desired target segment 172 of the vessel 170. This can be performed conventionally by introducing a guidewire 180 through the blood vessel 170 (FIG. 12A), and then introducing an introducer 480 in a conventional "over-the-wire" manner until its distal end resides just proximal to the target vessel segment 172 (FIG. 12B). The guidewire 180 is then removed from the catheter sheath 480, and then the catheter sheath 410, along with the catheter member 420 and laser fiber 228, is introduced through the introducer 480 until the distal end 234 of the laser fiber 228 resides within the distal end of the introducer 480 (FIG. 12C). The introducer 480 is then pulled proximally relative to the catheter assembly 402, which in turn, deploys the distal end of the catheter assembly 402 out from the introducer 480 (FIG. 12D).

Specifically, once the arms 434 and balloon 432 are released from the introducer 480, the compression exerted on the balloon 432 is minimized, thereby allowing the automated longitudinal translator 408, and specifically the spring 464, to urge the annular flange 460, and thus the catheter member 420, in the distal direction 132. As the annular flange 460 moves distally, the medium is conveyed from the annular cavity 436 into the balloon 432 via the lumen 438, which in turn, expands the balloon 432, hinging the arms 434 outward against the wall of the vessel 170.

The catheter assembly 402 can be introduced into the vessel 170 without the aid of the introducer 480 by ensuring that the arms 434 do not hinder distal movement of the catheter assembly 402 through the vessel 170. For example, the automated longitudinal translator 408 can be designed, such that when fully deployed, the balloon 432 does not expand the arms 434 against the wall of the vessel 170. As another example, the connector assembly 440 can include an inflation/deflation port (not shown) that is in fluid communication with the annular cavity 436 via an inflation/deflation lumen (not shown). In this case, prior to introducing the catheter assembly 402 into the vessel 170, the medium can be withdrawn from the annular cavity 436 via the inflation/deflation port (e.g., using a syringe) to deflate the balloon 432. Once the catheter assembly 402 is situated within the is vessel 170, and the distal end of the catheter assembly 402 is located adjacent the target segment 172 of the vessel 170, the medium is introduced into the annular cavity 436 via the inflation/deflation port to inflate the balloon 432.

Figure 12E:
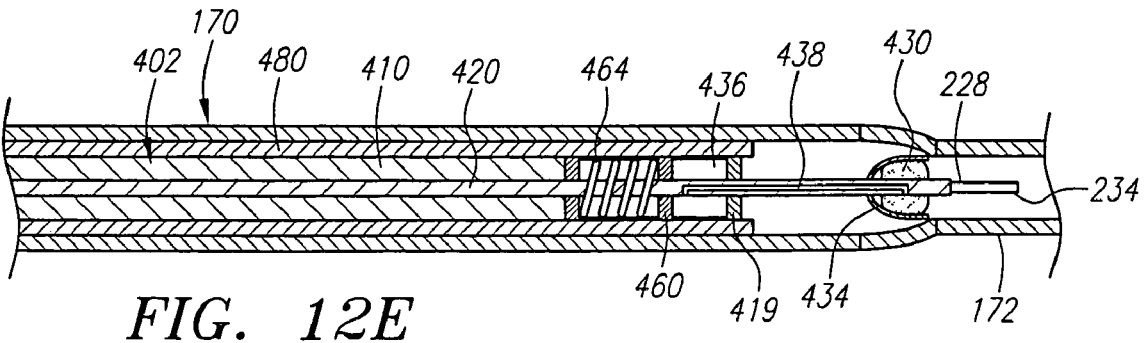

In any event, in order to stabilize the catheter sheath 410 relative to the patient's body, the connector sleeve 442 or otherwise the portion of the catheter sheath 410 residing outside of the blood vessel 170, is sutured, taped, or clamped to the patient just proximal to the entry site. The laser 206 is then coupled to the connector assembly 440. The laser 206 is then operated to convey laser energy to the distal end 234 of the laser fiber 228 to ablate the endothelial wall of the vessel segment 172, which after a period of time, results in the collapsing and occlusion of the vessel segment 172 (FIG. 12E). As the vessel segment 172 collapses, the arms 434 hinge inward, thereby collapsing the balloon 432, conveying the fluid from the balloon 432 into the annular cavity 436 via the lumen 438. As a result, pressure (feedback signal $S_{FEED}$) is exerted on the annular flange 460. Once the magnitude of the pressure exceeds the opposing spring force and any frictional forces (closed vessel threshold $S_{CLOSED}$), the annular flange 460, and thus the catheter member 420, moves in the proximal direction 134, thereby proximally translating the distal end 234 of the laser fiber 228 away from the closed vessel segment 172.

Figure 12F:
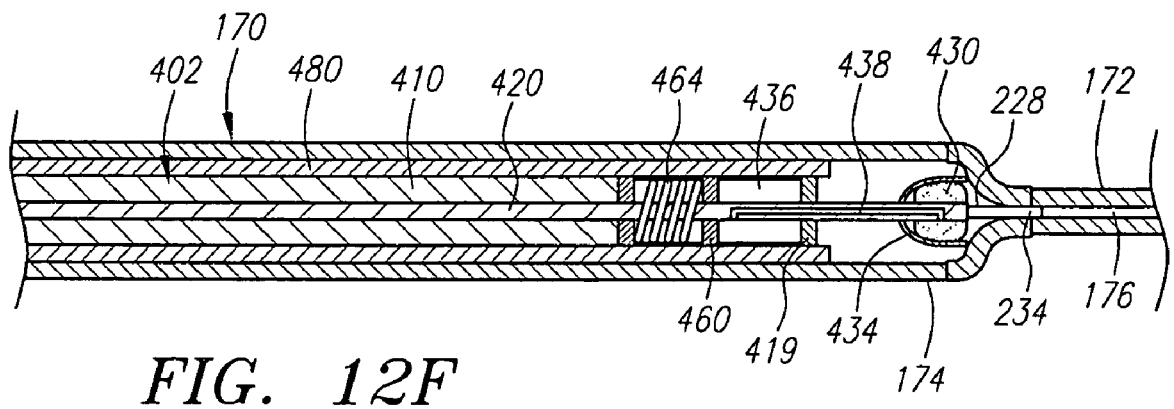
Figure 12G:
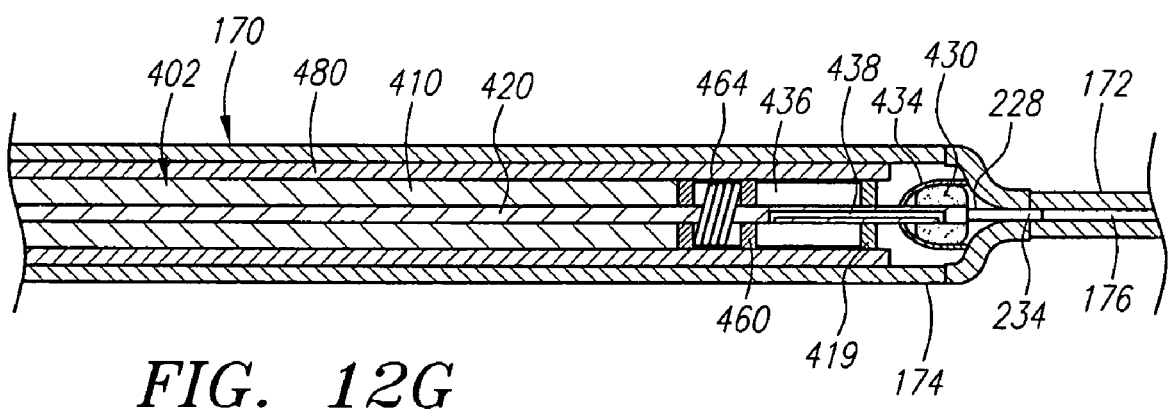

As the distal end 234 of the laser fiber 228 is moved away from the closed vessel segment 172 into the next proximal vessel segment 174, which is open, the compressive force on the balloon 432 is decreased. Once the pressure (feedback signal $S_{FEED}$) exerted on the annular flange 460 is equal to the opposing spring force and any frictional forces (open vessel threshold $S_{OPEN}$) exerted on the annular flange 460, the distal end 234 of the laser fiber 228 has moved completely out of the closed vessel segment 172 and into the next proximal vessel segment 174, and any further proximal movement of the annular flange 460, and thus the catheter member 420, ceases (FIG. 12F).

The vessel segment 172 will be highly thrombosed and totally or mostly occluded when the ablation electrode 128 is withdrawn. As with the operation of the previous devices, a small lumen 176 may remain in the closed vessel segment 172 where the distal end 234 of the laser fiber 228 had been deployed. Any such remaining lumen 176, however, will quickly occlude by normal inflammatory and clotting processes, thus assuring the closure of the vessel segment 172, as illustrated in FIG. 12F.

Figure 12H:
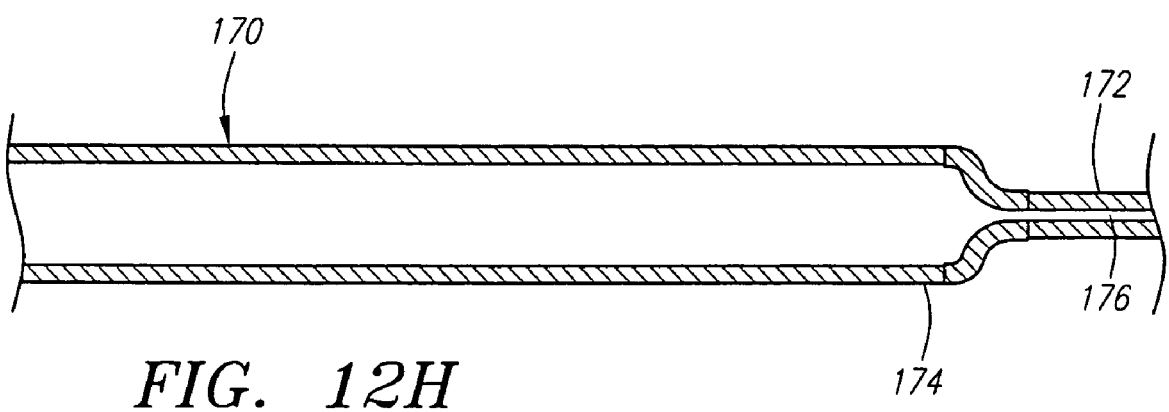

The process is repeated to occlude the next proximal vessel segment 176, and optionally more proximal segments, thereby forming a longitudinal occlusion 178 (FIG. 12G), and then the catheter assembly 402 is completely removed from the blood vessel 170 (FIG. 12H). Alternatively, the catheter assembly 402 is removed from the blood vessel 170 after the first vessel segment 172 has been occluded, thereby forming an acute point occlusion.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of occluding a vessel, comprising:
   ablating an endothelial wall of a vessel segment by activating one or more ablation elements;
   sensing a closing of the vessel segment by measuring a pressure applied by the endothelial wall of the vessel segment; and
   generating feedback indicating a state of closure of the vessel segment.

2. The method of claim 1, wherein the vessel is a blood vessel.

3. The method of claim 1, wherein the one or more ablation elements is a plurality of ablation elements.

4. The method of claim 1, wherein the endothelial vessel wall is ablated using radio frequency (RE) energy.

5. The method of claim 1, wherein the endothelial vessel wall is ablated using laser energy.

6. The method of claim 1, wherein the endothelial vessel wall is ablated using a chemical solution.

7. The method of claim 1, wherein the closing of the vessel segment is sensed by sensing a strain.

8. The method of claim 1, further comprising comparing the sensed vessel segment closure state to a closed vessel threshold.

9. The method of claim 8, further comprising comparing the sensed vessel segment closure state to an open vessel threshold.

10. A method of occluding a vessel, comprising:
    ablating an endothelial wall of a vessel segment by activating one or more ablation elements;
    sensing a closing of the vessel segment;

generating feedback indicating a state of closure of the vessel segment;

automatically longitudinally translating the one or more ablation elements relative to the vessel segment based on the feedback.

11. The method of claim 10, wherein the vessel is a blood vessel.

12. The method of claim 10, wherein the one or more ablation elements is a plurality of ablation elements.

13. The method of claim 10, wherein the endothelial vessel wall is ablated using radio frequency (RF) energy.

14. The method of claim 10, wherein the endothelial vessel wall is ablated using laser energy.

15. The method of claim 10, wherein the endothelial vessel wall is ablated using a chemical solution.

16. The method of claim 10, wherein the closing of the vessel segment is sensed by sensing a strain.

17. The method of claim 10, wherein the one or more ablation elements is translated in the proximal direction.

18. The method of claim 10, further comprising comparing the sensed vessel segment closure state to a closed vessel threshold, wherein the one or more ablation elements is translated in a proximal direction when the vessel segment closure state equals the closed vessel threshold.

19. The method of claim 18, further comprising comparing the sensed vessel segment closure state to an open vessel threshold, wherein the longitudinal translation of the one or more ablation elements in the proximal direction is ceased when the vessel segment closure state equals the vessel open threshold.

20. The method of claim 10, wherein the one or more ablation elements is translated to another vessel segment, and the endothelial wall ablation, vessel segment closure sensing, feedback generation, and automatic longitudinal translation are repeated to provide a longitudinal occlusion of the vessel.

* * * * *